United States Patent
Butt et al.

(10) Patent No.: US 11,872,694 B2
(45) Date of Patent: *Jan. 16, 2024

(54) APPARATUS AND METHOD FOR CONTROLLING AN END-EFFECTOR ASSEMBLY

(71) Applicant: Titan Medical Inc., Toronto (CA)

(72) Inventors: Eric Butt, Orange, CT (US); Jeff Ransden, Fairfield, CT (US); Alexander Shvartsberg, Oakville (CA); Reiza Rayman, Toronto (CA)

(73) Assignee: Titan Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/164,479

(22) Filed: Feb. 3, 2023

(65) Prior Publication Data

US 2023/0256627 A1     Aug. 17, 2023

Related U.S. Application Data

(63) Continuation of application No. 16/676,311, filed on Nov. 6, 2019, now Pat. No. 11,571,820, which is a
(Continued)

(51) Int. Cl.
     *B25J 18/00*         (2006.01)
     *A61B 34/00*         (2016.01)
     (Continued)

(52) U.S. Cl.
     CPC .............. *B25J 18/00* (2013.01); *A61B 34/70* (2016.02); *A61B 2017/00309* (2013.01);
(Continued)

(58) Field of Classification Search
     CPC .... B25J 18/00; B25J 15/0206; B25J 15/0213; A61B 34/70; A61B 2034/301;
(Continued)

(56) References Cited

U.S. PATENT DOCUMENTS

| | | |
|---|---|---|
| 3,115,140 A | 12/1963 | Volkman |
| 3,196,875 A | 7/1965 | Pfeiffer |

(Continued)

FOREIGN PATENT DOCUMENTS

| | | |
|---|---|---|
| CA | 1239167 A | 7/1988 |
| CA | 2222150 C | 9/2008 |

(Continued)

OTHER PUBLICATIONS

Corresponding PCT Application No. PCT/CA2011/001225 International Search Report dated Jul. 26, 2012.
(Continued)

*Primary Examiner* — Zoheb S Imtiaz
(74) *Attorney, Agent, or Firm* — Knobbe, Martens, Olson & Bear LLP

(57) ABSTRACT

An apparatus for controlling an end-effector assembly is provided. The apparatus includes a elongated element configured to engage the end-effector assembly and a drive assembly. A first motion transfer mechanism is disposed at an end of the elongated element. The first motion transfer mechanism is configured to transfer a rotational motion of the elongated element to a motion of the end-effector assembly. A second motion transfer mechanism is disposed at the second end of the elongated element. The second motion transfer mechanism is configured to transfer a motion of the drive assembly to the rotational motion of the elongated element.

19 Claims, 25 Drawing Sheets

Related U.S. Application Data continuation of application No. 14/262,221, filed on Apr. 25, 2014, now Pat. No. 10,471,607, which is a continuation of application No. PCT/CA2011/001225, filed on Nov. 4, 2011.

(51) Int. Cl.
  *B25J 15/02* (2006.01)
  *A61B 34/30* (2016.01)
  *A61B 17/00* (2006.01)
  *A61B 17/29* (2006.01)

(52) U.S. Cl.
  CPC ............... *A61B 2017/00314* (2013.01); *A61B 2017/00526* (2013.01); *A61B 2017/2905* (2013.01); *A61B 2017/2908* (2013.01); *A61B 2017/2927* (2013.01); *A61B 2034/301* (2016.02); *A61B 2034/305* (2016.02); *B25J 15/0206* (2013.01); *B25J 15/0213* (2013.01); *Y10S 901/23* (2013.01); *Y10T 74/20311* (2015.01); *Y10T 74/20329* (2015.01)

(58) Field of Classification Search
  CPC .... A61B 2034/305; A61B 2017/00309; A61B 2017/00314; A61B 2017/00526; A61B 2017/2905; A61B 2017/2908; A61B 2017/2927; Y10T 74/20311; Y10T 74/20329; Y10S 901/23
  See application file for complete search history.

(56) References Cited

U.S. PATENT DOCUMENTS

| | | | |
|---|---|---|---|
| 3,227,290 | A | 1/1966 | Lemelson |
| 3,272,347 | A | 9/1966 | Lemelson |
| 3,922,930 | A | 12/1975 | Fletcher |
| 4,645,409 | A | 2/1987 | Gorman |
| 4,897,014 | A | 1/1990 | Tietze |
| 5,201,742 | A | 4/1993 | Hasson |
| 5,279,309 | A | 1/1994 | Taylor et al. |
| 5,347,997 | A | 9/1994 | Weiler et al. |
| 5,382,885 | A | 1/1995 | Salcudean et al. |
| 5,390,678 | A | 2/1995 | Gesswein |
| 5,403,332 | A | 4/1995 | Christoudias |
| 5,665,095 | A | 9/1997 | Jacobson |
| 5,749,362 | A | 5/1998 | Funda et al. |
| 5,827,323 | A | 10/1998 | Klieman |
| 5,891,020 | A | 4/1999 | Luber et al. |
| 6,132,368 | A | 10/2000 | Cooper |
| 6,245,028 | B1 | 6/2001 | Furst et al. |
| 6,264,665 | B1 | 7/2001 | Yu et al. |
| 6,299,625 | B1 | 10/2001 | Bacher |
| 6,471,172 | B1 | 10/2002 | Lemke |
| 6,506,208 | B2 | 1/2003 | Hunt |
| 6,620,173 | B2 | 9/2003 | Gerbi et al. |
| 6,666,554 | B2 | 12/2003 | Mulvey |
| 6,673,092 | B1 | 1/2004 | Bacher |
| 6,685,698 | B2 | 2/2004 | Morley et al. |
| 6,699,177 | B1 | 3/2004 | Wang et al. |
| 7,048,745 | B2 | 5/2006 | Tierney et al. |
| 7,118,582 | B1 | 10/2006 | Wang et al. |
| 7,331,967 | B2 | 2/2008 | Lee et al. |
| 7,419,080 | B2 | 9/2008 | Smith et al. |
| 7,428,491 | B2 | 9/2008 | Wang et al. |
| 7,540,867 | B2 | 6/2009 | Jinno |
| 7,608,083 | B2 | 10/2009 | Lee et al. |
| 7,666,191 | B2 | 2/2010 | Orban, III et al. |
| 7,695,481 | B2 | 4/2010 | Wang et al. |
| 7,867,241 | B2 | 1/2011 | Brock et al. |
| 7,918,826 | B2 | 4/2011 | Armstrong et al. |
| 7,942,895 | B2 | 5/2011 | Jinno |
| 7,963,913 | B2 | 6/2011 | Devengenzo et al. |
| 8,920,433 | B2 | 12/2014 | Barrier |
| 10,004,524 | B2 | 6/2018 | Karcher |
| 2002/0007188 | A1 | 1/2002 | Arambula et al. |
| 2002/0074463 | A1 | 6/2002 | Nakamura |
| 2003/0229338 | A1 | 12/2003 | Irion et al. |
| 2004/0009459 | A1 | 1/2004 | Anderson et al. |
| 2005/0080333 | A1 | 4/2005 | Piron et al. |
| 2006/0050239 | A1 | 3/2006 | Hashimoto |
| 2006/0161039 | A1 | 7/2006 | Juliana et al. |
| 2006/0161136 | A1 | 7/2006 | Anderson et al. |
| 2006/0235436 | A1 | 10/2006 | Anderson et al. |
| 2007/0088340 | A1 | 4/2007 | Brock et al. |
| 2007/0208375 | A1 | 9/2007 | Nishizawa et al. |
| 2008/0033410 | A1 | 2/2008 | Rastegar et al. |
| 2008/0147089 | A1 | 6/2008 | Loh et al. |
| 2008/0213077 | A1 | 9/2008 | Tanaka et al. |
| 2008/0232932 | A1* | 9/2008 | Jinno ..................... A61B 34/74 901/38 |
| 2009/0041565 | A1 | 2/2009 | Rodriguez Y Baena |
| 2009/0095790 | A1 | 4/2009 | Whitman |
| 2009/0101692 | A1 | 4/2009 | Whitman |
| 2009/0171185 | A1 | 7/2009 | Chou et al. |
| 2009/0234444 | A1 | 9/2009 | Maschke |
| 2009/0248039 | A1 | 10/2009 | Cooper et al. |
| 2010/0042142 | A1 | 2/2010 | Cunningham |
| 2010/0268249 | A1 | 10/2010 | Stuart |
| 2011/0071543 | A1 | 3/2011 | Prisco et al. |
| 2011/0174860 | A1 | 7/2011 | Shelton, IV et al. |
| 2011/0277775 | A1 | 11/2011 | Holop et al. |
| 2012/0150154 | A1 | 6/2012 | Brisson |
| 2012/0234893 | A1* | 9/2012 | Schuckmann ... A61B 17/07207 227/175.2 |
| 2013/0053866 | A1 | 2/2013 | Leung et al. |
| 2013/0099072 | A1 | 4/2013 | Buller et al. |
| 2013/0199540 | A1 | 8/2013 | Buske |
| 2014/0276931 | A1* | 9/2014 | Parihar ................... A61B 34/30 606/130 |
| 2016/0303745 | A1 | 10/2016 | Rockrohr |
| 2017/0151013 | A1* | 6/2017 | Kappus ............. A61B 18/1206 |

FOREIGN PATENT DOCUMENTS

| | | |
|---|---|---|
| EP | 1886633 A2 | 2/2008 |
| EP | 2366342 A1 | 9/2011 |
| GB | 2239605 A | 7/1991 |
| JP | 20078017903 A | 1/2008 |
| SU | 1299676 A1 | 3/1987 |
| WO | WO 98/25666 A1 | 6/1998 |
| WO | WO 00/30548 A1 | 6/2000 |
| WO | WO 2004070400 A1 | 8/2004 |
| WO | WO 2009157719 A2 | 12/2009 |
| WO | WO 2010090292 A2 | 8/2010 |
| WO | WO 2011013103 | 2/2011 |

OTHER PUBLICATIONS

Corresponding PCT Application No. PCT/CA2011/001225 Written Opinion of the International Searching Authority dated Jul. 26, 2012.
Non-Final Rejection dated May 5, 2017 for U.S. Appl. No. 14/279,828.
Related PCT Application No. PCT/CA2011/001302 International Search Report dated Aug. 31, 2012.
Related PCT Application No. PCT/CA2011/001302 Written Opinion of the International Searching Authority dated Aug. 31, 2012.
Related PCT Application No. PCT/CA2011/001303 International Search Report dated Aug. 17, 2012.
Related PCT Application No. PCT/CA2011/001303 Written Opinion of the International Searching Authority dated Aug. 17, 2012.
Related PCT Application No. PCT/CA2011/001386 International Search Report dated Aug. 13, 2012.
Related PCT Application No. PCT/CA2011/001386 Written Opinion of the International Searching Authority dated Aug. 13, 2012.
Related PCT Application No. PCTCA2011/001226 International Search Report dated Jul. 17, 2012.

(56) References Cited

OTHER PUBLICATIONS

Related PCT Application No. PCTCA2011/001226 Written Opinion of the International Searching Authority dated Jul. 17, 2012.

* cited by examiner

APPARATUS AND METHOD FOR CONTROLLING AN END-EFFECTOR ASSEMBLY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

The present specification here relates in general to a field of robotic instruments, and more particularly, to a robotic system for use in surgery.

BACKGROUND

With the gradual transition of medical surgery from the conventional process of making a long incision in the patient's body for performing a surgery to the next generation of surgery, i.e. minimal invasive surgery (MIS), continuous research is going on to develop and integrate robotic instruments in a system which can be used for MIS purposes. Such integration can help a surgeon perform a surgery in a substantially error-free manner, and at the same time work in a realistic environment that gives the surgeon a feel of conventional surgery.

SUMMARY

In accordance with an aspect of the invention, there is provided an apparatus for controlling an end-effector assembly. The apparatus includes a first elongated element having a first end and a second end. The first end of the first elongated element is configured to engage the end-effector assembly. The second end of the first elongated element is configured to engage a drive assembly. The apparatus further includes a first motion transfer mechanism disposed at the first end of the first elongated element. The first motion transfer mechanism is configured to transfer a rotational motion of the first elongated element to a first motion of the end-effector assembly. Furthermore, the apparatus includes a second motion transfer mechanism disposed at the second end of the first elongated element. The second motion transfer mechanism is configured to transfer a first motion of the drive assembly to the rotational motion of the first elongated element.

The apparatus may further include a second elongated element having first and second ends. The first end of the second elongated element may be configured to engage the end-effector assembly. The second end of the second elongated element may be configured to engage the drive assembly.

The second elongated element may be configured to adjust a roll of the end-effector assembly.

The apparatus may further include a third motion transfer mechanism disposed at the first end of the second elongated element. The third motion transfer mechanism may be configured to transfer a rotational motion of the second elongated element to a second motion of the end-effector assembly. The apparatus may also include a fourth motion transfer mechanism disposed at the second end of the second elongated element. The fourth motion transfer mechanism may be configured to transfer a second motion of the drive assembly to the rotational motion of the second elongated element.

The first elongated element may include a first tube.

The second elongated element may include a second tube.

The first elongated element may be nested within the second tube.

The first elongated element may be configured to rotate independently from the second tube.

The first motion transfer mechanism of the first elongated element may include a plurality of teeth.

The plurality of teeth of the first elongated element may be configured to mate with a first plurality of teeth of the end-effector assembly.

The third motion transfer mechanism of the second elongated element may include a plurality of teeth.

The plurality of teeth of the second elongated element may be configured to mate with a second plurality of teeth of the end-effector assembly.

The first elongated element may include a flexible portion.

The first elongated element may include stainless steel.

The flexible portion of the first elongated element may be laser cut to increase flexibility.

The second elongated element may include a flexible portion.

The second elongated element may include stainless steel.

The flexible portion of the second elongated element may be laser cut to increase flexibility.

The apparatus may further include a third elongated element having first and second ends. The first end of the third elongated element may be configured to engage the endeffector assembly. The second end of the third elongated element may be configured to engage the drive assembly.

The third elongated element may be configured to adjust a roll of the end-effector assembly.

The third elongated element may include a third tube.

The first and second elongated elements may be nested within the third tube.

The first elongated element may be configured to rotate independently from the third tube.

The apparatus may be configured to provide a coarse motion proximate to the end-effector assembly.

The apparatus may further include a plurality of cables to control the coarse motion.

The apparatus may further include a rigid outer cover.

The rigid outer cover may be fixed.

The plurality of cables may be disposed between the rigid outer cover and the first elongated element.

The apparatus may further include an electrical wire extending through the first tube.

At least one elongated element may be electrically conductive.

In accordance with another aspect of the invention, there is an end-effector assembly. The assembly includes a first working member configured to engage a first elongated element. Furthermore, the assembly includes a motion transfer mechanism disposed on the first working member. The motion transfer mechanism is configured to transfer a rotational motion of the first elongated element to a motion of the first working member.

The assembly may further include a connector. The connector may be configured to connect to a second elongated element. The second elongated element may provide a rotational motion to adjust a roll of the end-effector assembly.

The assembly may further include a second working member configured to engage a second elongated element. In addition, the assembly may further include a motion transfer mechanism disposed on the second working member. The motion transfer mechanism mat be configured to transfer a rotational motion of the second elongated element to a motion of the second working member.

The motion transfer mechanism of the first working member may include a plurality of teeth.

The plurality of teeth of the first working member may be configured to mate with a plurality of teeth of the first elongated element.

The motion transfer mechanism of the second working member may include a plurality of teeth.

The plurality of teeth of the second working member may be configured to mate with a plurality of teeth of the second elongated element.

The first working member may include a first jaw.

The motion of the first working member may include opening and closing the first jaw.

The second working member may include a second jaw.

The motion of the second working member may include opening and closing the second jaw.

In accordance with another aspect of the invention, there is provided a drive assembly configured to connect to a rotatable elongated element. The drive assembly includes a drive mechanism configured to engage the rotatable elongated element. Furthermore, the drive assembly includes a motion transfer mechanism disposed on the drive mechanism. The motion transfer mechanism is configured to transfer a motion of the drive mechanism to a rotational motion of the rotatable elongated element.

The motion transfer mechanism may include a plurality of teeth.

The plurality of teeth may be configured to mate with a plurality of teeth of the rotatable elongated element.

The drive mechanism may include an electric motor.

In accordance with another aspect of the invention, there is provided a robotic instrument having first and second ends. The robotic instrument includes an end-effector assembly disposed at the first end of the robotic instrument, the end-effector assembly comprising a first working member. Furthermore, the robotic instrument includes a drive assembly disposed at the second end of the robotic instrument. In addition, the robotic instrument includes a first elongated element having a first end and a second end, the first end of the first elongated element engaged with the end-effector assembly and the second end of the first elongated element engaged with a drive assembly such that rotation of the first elongated element causes the first working member of the end-effector assembly to move.

The robotic instrument may further include a second elongated element having first and second ends. The first end of the second elongated element may be engaged with the end-effector assembly. The second end of the second elongated element may be engaged with the drive assembly.

Rotation of the second elongated element may adjust a roll of the end-effector assembly.

The end-effector assembly may further include a second working member.

Rotation of the second elongated element may cause the second working member of the end-effector assembly to move.

The first elongated element may include a first tube.

The second elongated element may include a second tube.

The first elongated element may be nested within the second tube.

The first elongated element may be connected to the end-effector assembly with a gear mechanism.

The second elongated element may be connected to the end-effector assembly with a gear mechanism.

The first elongated element may include a flexible portion.

The first elongated element may include stainless steel.

The flexible portion of the first elongated element may be laser cut to increase flexibility.

The second elongated element may include a flexible portion.

The second elongated element may include stainless steel.

The flexible portion of the second elongated element may be laser cut to increase flexibility.

The robotic instrument may further include a third elongated element having first and second ends. The first end of the third elongated element may be configured to engage the end-effector assembly. The second end of the third elongated element may be configured to engage the drive assembly.

The third elongated element may be configured to adjust a roll of the end-effector assembly.

The third elongated element may include a third tube.

The first and second elongated elements may be nested within the third tube.

The robotic instrument may be configured to provide a coarse motion proximate to the end-effector assembly.

The robotic instrument may further include a plurality of cables to control the coarse motion.

The robotic instrument may further include a rigid outer cover.

The rigid outer cover may be fixed.

The plurality of cables may be disposed between the rigid outer cover and the first elongated element.

The robotic instrument may further include an electrical wire extending through the first tube.

At least one elongated element may be electrically conductive.

The robotic instrument may further include a fixed outer cover.

In accordance with an aspect of the invention, there is provided a method for controlling an end-effector assembly at the end of a robotic instrument. The method involves rotating a first elongated element using a drive assembly, wherein the first elongated element is engaged with the drive assembly. The method further involves transferring a rotational motion of the first elongated element to move a first working member of the end-effector assembly.

The method may further involve rotating a second elongated element using the drive assembly. The second elongated element may be engaged with the drive assembly.

Rotating the second elongated element may adjust a roll of the end-effector assembly.

Rotating the second elongated element may move a second working member of the end-effector assembly.

Rotating a first elongated element may involve rotating a first tube.

Rotating a second elongated element may involve rotating a second tube.

The first elongated element may be nested within the second tube.

The method may further involve flexing a flexible portion of the first elongated element.

The first elongated element may include stainless steel.

The flexible portion of the first elongated element may be laser cut to increase flexibility.

The method may further involve flexing a flexible portion of the second elongated element.

The second elongated element may include stainless steel.

The flexible portion of the second elongated element may be laser cut to increase flexibility.

The method may further involve rotating a third elongated element using the drive assembly. The third elongated element may be engaged with the drive assembly and wherein rotating the third elongated element adjusts a roll of the end-effector assembly.

The third elongated element may include a third tube.

The first and second elongated elements may be nested within the third tube.

The method may further involve controlling a coarse motion of the first end of the first elongated element.

Controlling may involve applying tension to a plurality of cables.

BRIEF DESCRIPTION OF THE DRAWINGS

Reference will now be made, by way of example only, to the accompanying drawings in which.

DETAILED DESCRIPTION OF THE EMBODIMENTS

Figure 1:
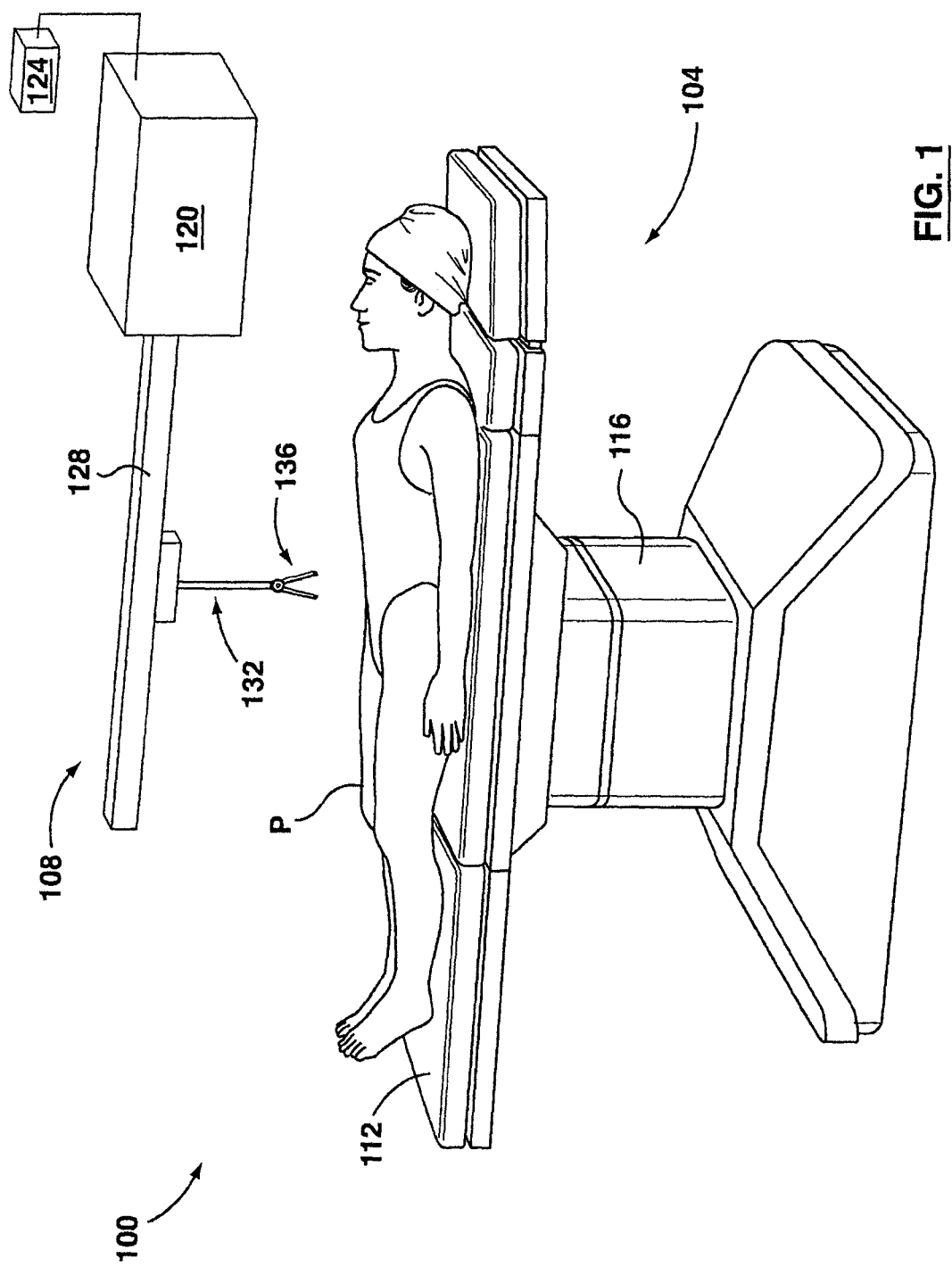
FIG. 1 is a perspective view of an operating theater according to an embodiment.

Referring to FIG. 1, a schematic representation of an operating theater for Minimal Invasive Surgery (MIS) is shown at 100. It is to be understood that the operating theater 100 is purely exemplary and it will be apparent to those skilled in the art that a variety of operating theaters are contemplated. The operating theater 100 includes a surgical table 104 and a surgical system 108. The surgical table 104 includes a surface 112 supported by a base 116. It is to be understood that the surgical table 104 is not particularly limited to any particular structural configuration. A patient P rests on the surface 112. The surgical system 108 includes a base unit 120, an input device 124, a robotic arm 128, and at least one robotic instrument 132 with an end-effector assembly 136.

In a present embodiment, the base unit 120 is generally configured to support and control the robotic arm 128 in response to input control signals from input device 124 under the control of a surgeon or other medical professional. In terms of providing physical support, the base unit 120 is mechanically structured to support the robotic arm 128, the robotic instrument 132, and their associated movements. For example, the base unit 120 can be bolted to a fixed structure such as a wall, floor, or ceiling. Alternatively, the base unit 120 can have a mass and a geometry such that when base unit 120 is free-standing, it will support the robotic arm 128. In some embodiments, the base unit 120 can include a moveable cart to provide easy movement of the base unit 120 around the operating theater 100. In terms of providing control, the base unit 120 can include mechanical controls (not shown), or electrical controls (not shown), or both. For example, mechanical controls can include gears, cables or other motion transfer mechanisms (not shown) connected to a motor. Other mechanical controls can also involve hydraulics. Alternatively, in embodiments where a motor is disposed in the robotic arm 128 or the robotic instrument 132, the base unit 120 can supply only electrical control signals to operate the motors in the robotic arm 128 or the robotic instrument 132.

Referring again to FIG. 1, the robotic arm 128 is generally configured to support the robotic instrument 132. In terms of providing physical support, the robotic arm 128 is mechanically structured to support the robotic instrument 132, and its associated movement. For example, the robotic arm 128 is constructed such that it is rigid enough to be suspended above the patient P. In addition, the robotic arm 128 can be configured so that robotic instrument 132 is positionable in relation to the base unit 120 and surface 112. For example, the robotic arm 128 can include a moveable joint (not shown) for providing a pivotal degree of freedom. In another example, the robotic arm 128 can include a rail system (not shown) for linear movement of the robotic instrument 132. It will now be understood that the movement of the robotic arm 128 is controlled by the base unit 120 through various controls described above.

In general terms, the robotic instrument 132 and its end-effector assembly 136 are generally configured for performing MIS responsive to inputs from the input device 124 mediated by the base unit 120 and the robotic arm 128. However, it is to be re-emphasized that the structure shown in FIG. 1 is a schematic, non-limiting representation only. For example, although only one robotic arm 128 is shown in FIG. 1, it is to be understood that the surgical system 108 can be modified to include a plurality of robotic arms 128, each robotic arm 128 having its own a separate robotic instrument 132 and separate end-effector assembly 136. Furthermore, it is also to be understood that where the surgical system 108 includes a plurality of robotic arms 128 with robotic instruments 132, each robotic arm 128 or robotic instrument 132 can have different structures. Indeed, a plurality of different configurations of robotic instrument 132 are contemplated herein.

In use, the robotic instrument 132 is configured to provide the end-effector assembly 136 with at least one degree of freedom. A degree of freedom refers to an ability of an endeffector assembly 136 to move according to a specific motion. For example, a degree of freedom can include a rotation of the end-effector assembly 136 or a component thereof about a single axis. Therefore, for each axis of rotation, the end-effector assembly 136 is said to have a unique degree of freedom. Another example of a degree of freedom can include a translational movement along a path. It will now be apparent that each additional degree of freedom increases the versatility of the end-effector assembly 136. By providing more degrees of freedom, it will be possible to position the end-effector assembly 136 in a wider variety of positions or locations to, for example, reach around obstacles.

Figure 2:
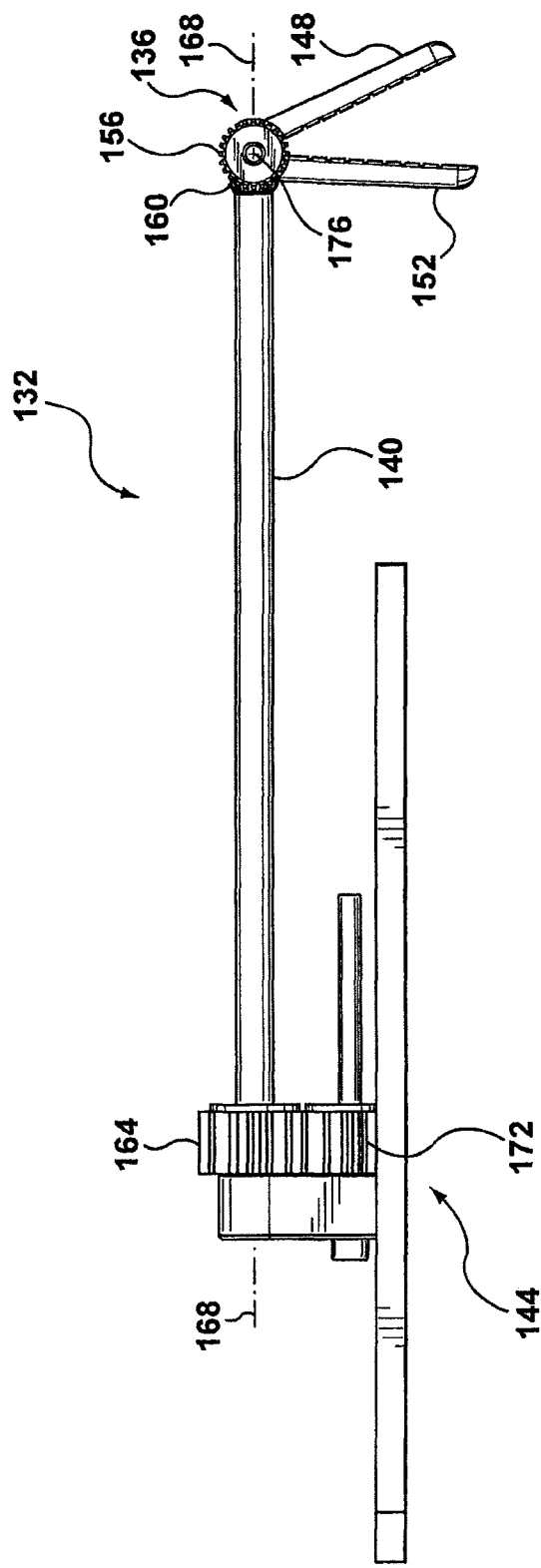
FIG. 2 is a perspective view of a robotic instrument in accordance with an embodiment.

Referring to FIG. 2, an embodiment of the robotic instrument 132 is shown in greater detail. It is to be understood that the robotic instrument 132 is purely exemplary and it will be apparent to those skilled in the art that a variety of robotic instruments are contemplated including other embodiments discussed in greater detail below. The robotic instrument 132 includes an end-effector assembly 136, an elongated element 140 and a drive assembly 144.

Figure 3:
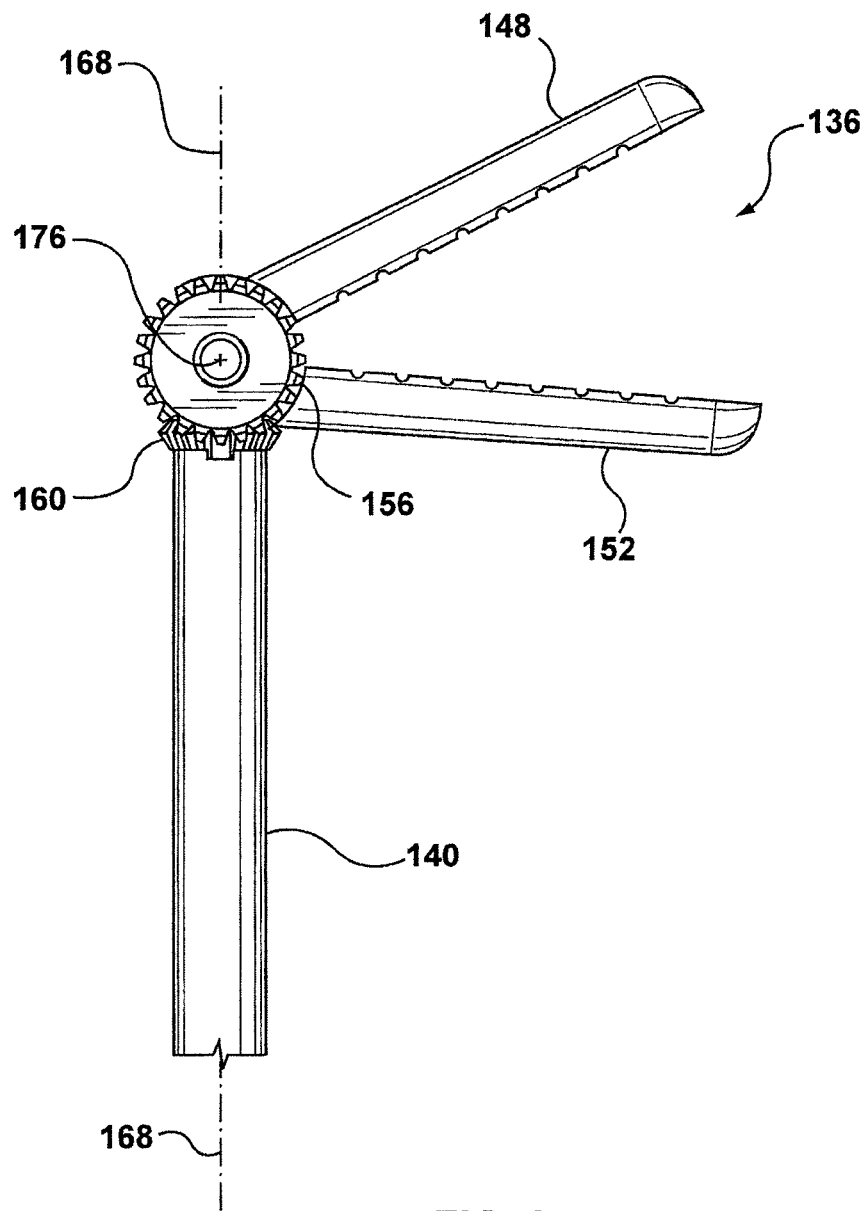
FIG. 3 is another perspective view of the robotic instrument with the working member in an open position in accordance with the embodiment of FIG. 2.

In the present embodiment, the end-effector assembly 136 is shown in FIG. 3. The end-effector assembly 136 is generally configured to interact with the patient P during MIS. The end-effector assembly 136 includes two working members 148 and 152. The end-effector assembly 136 also includes a motion transfer mechanism. In the present embodiment, the transfer mechanism is a gear 156 having a plurality of teeth. In particular, the gear 156 of the present embodiment is a bevel gear. However, other embodiments may use other types of gears. It is to be understood that the end-effector assembly 136, including the working members 148 and 152, is not particularly limited to any material and that several different types of materials are contemplated. The end-effector assembly 136 is typically constructed from materials which can withstand the harsh conditions of a sterilization process carried out prior to an actual surgery. Some examples of suitable materials include stainless steel, such as surgical stainless steel, titanium, plastics, composites and other materials commonly used in surgical instruments. The exact configuration of working members 148 and 152 is not particularly limited. In the present embodiment shown in FIGS. 2-4, the working members 148 and 152 are the jaws of forceps. In other embodiments, the working members can be other surgical instruments such as scissors, blades, graspers, clip appliers, staplers, retractors, clamps or bipolar cauterizers or combinations thereof. Also, in other embodiments the end-effector assembly may include a single working member such as imaging equipment, such as a camera or light source, or surgical instruments such as scalpels, hooks, needles, catheters, spatulas or mono-polar cauterizers.

Referring again to FIG. 2, the elongated element 140 extends between the endeffector assembly 136 and the drive assembly 144. The elongated element 140 is generally configured to support and control the end-effector assembly 136. It is to be understood that the elongated element 140 is not particularly limited to any material and that several different types of surgical-grade materials are contemplated. Examples of surgical grade materials include surgical stainless steel, titanium, plastics, composites and other materials commonly used in surgery, which in general can withstand sterilization. The elongated element 140 includes two motion transfer mechanisms. In the present embodiment, the motion transfer mechanisms include first and second gears 160 and 164 (FIG. 4) each having a plurality of teeth and disposed at opposite ends of the elongated element 140. The first gear 160 is configured to mate with the gear 156 of the end-effector assembly 136. In certain embodiments, the elongated element 140 is rigid, such that applying a rotational torque about an axis 168 at the second gear 164 will cause the elongated element 140 to rotate without significant deformation at the first gear 160. It will now be appreciated that the first gear 160 is configured to transfer rotational motion of the elongated element 140 to the gear 156 of the end-effector assembly 136 to move the working member 148.

Figure 4:
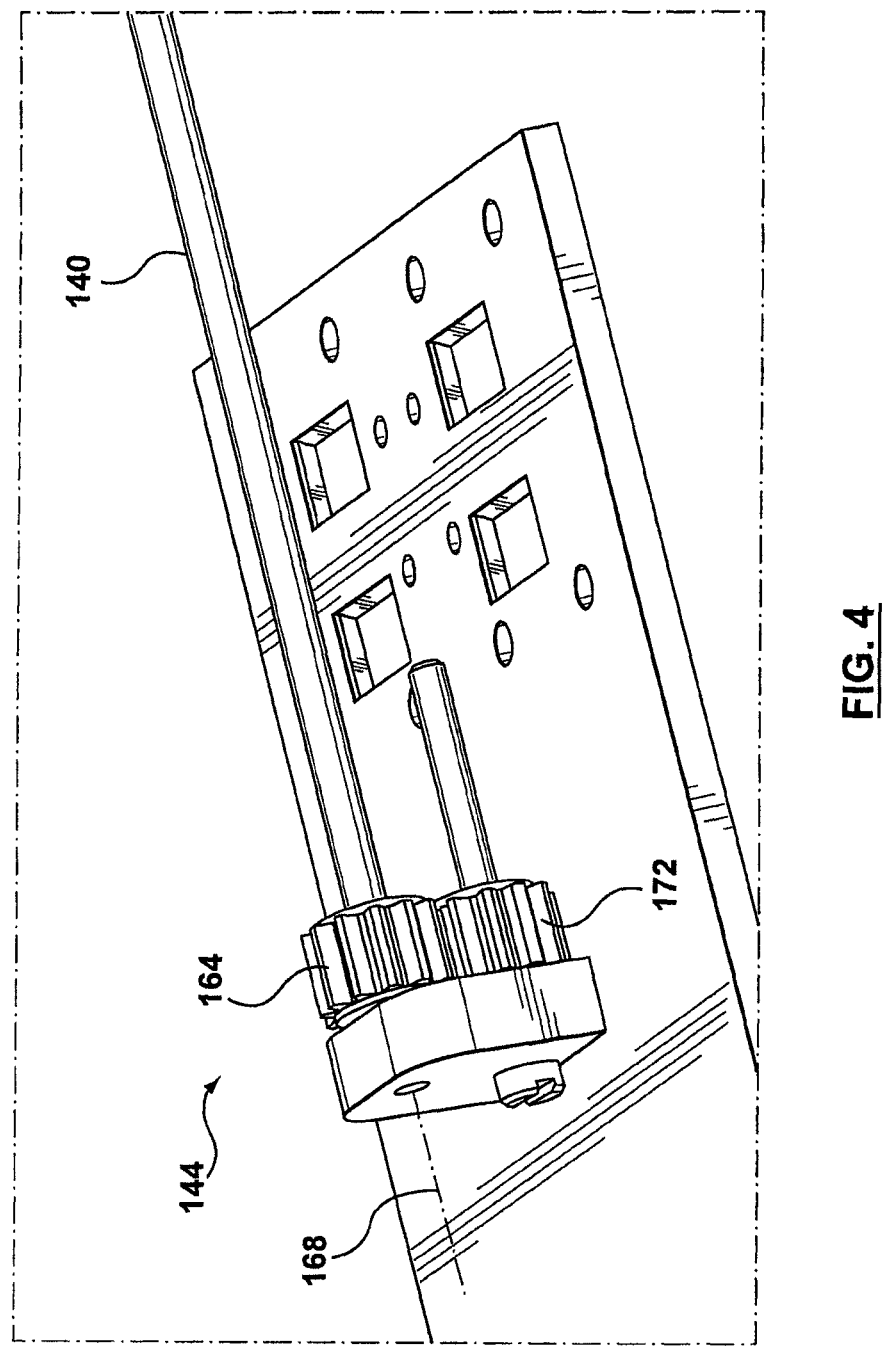
FIG. 4 is perspective view of a drive assembly of the robotic instrument in accordance with the embodiment of FIG. 2.

The drive assembly 144 of the present embodiment is shown in greater detail in FIG. 4. The drive assembly 144 includes a motion transfer mechanism. In the present embodiment, the transfer mechanism is a drive gear 172 having a plurality of teeth. The drive gear 172 is configured to mate with the second gear 164 of the elongated element 140. It will now be appreciated that the drive gear 172 is configured to transfer motion from the drive assembly 144 to a rotational motion of the elongated element 140 about the axis 168 by applying a rotational torque to the second gear 164 of the elongated element 140. The drive gear 172 can be driven by various means, such as via an electric motor (not shown), hydraulics, pneumatics, magnetic actuators or a piezoelectric motor. It will now be appreciated that the motion used to rotate the drive gear 172 does not need to be a rotational motion and can be any type of motion capable of applying a torque to rotate the drive gear 172.

In operation, the present embodiment of the robotic instrument 132 controls the movement of the working member 148 of the end-effector assembly 136. A source of motion in the drive assembly rotates the drive gear 172. The drive gear 172 engages the second gear 164 of the elongated element 140. Therefore, as the drive gear 172 is rotated, engagement to second gear 164 of the elongated element 140 will cause the elongated element to rotate about the axis 168. The rotation of the elongated element 140 will cause a corresponding rotation of the first gear 160. The first gear 160 engages the gear 156 of the end-effector assembly 136. Therefore, as the first gear 160 rotates, engagement to the gear 156 of the end-effector assembly 136 will cause the working member 148 to pivot about a first axis 176 to open and close the jaw. It will now be appreciated by a person skilled in the art with the benefit of this description and the accompanying drawings that the working member 152 can be fixed or can also be pivoted about the first axis 176. When the working member 152 is controlled by the elongated element 140, rotating the elongated element 140 can cause the working members 148 and 152 to open or close. For example, if the first gear 160 engages both working members 148 and 152 on opposite sides of the first gear 160, the first gear 160 can apply opposite torques to working members 148 and 152 about the first axis 176. By applying opposite torques, the working members 148 and 152 may be opened and closed by rotating the elongated element 140. It is to be understood that when both working members 148 and 152 are controlled by the elongated element 140, the working members 148 and 152 will close at the same position relative to the elongated element 140.

Therefore, in embodiments of end-effector assemblies comprising at least one jaw, such as the present embodiment, the first motion is characterized by the rotation motion within the same plane in which a jaw opens and closes.

It will now be appreciated that the first rotational motion provides a degree of freedom which involves rotating the end-effector assembly 136 about a first axis 176. However, it will now be appreciated that the first axis 176 will be substantially perpendicular to the axis 168 nearest to the first axis 176. In other words, the first axis 176 is not necessarily fixed with respect to the surface 112 or the surgical system 108.

In general terms, the robotic instrument 132 is generally configured to transfer a motion from a source in the drive assembly 144 to control the working member 148 of the endeffector assembly 136. It is to be re-emphasized that the structure shown in FIGS. 2 to 4 is a non-limiting representation only. Notwithstanding the specific example, it is to be understood that other mechanically equivalent structures and motion transfer mechanisms can be devised to perform the same function as the robotic instrument 132. For example, other motion transfer mechanisms can include frictional engagement, belts, or cables or combinations thereof. Furthermore, although the motion of the drive gear 172 is a rotational motion, it is not necessary that this be a rotational motion as discussed above. Other types of motion, such as a linear motion, are also contemplated. Furthermore, in some embodiments, the drive gear 172 and the second gear 164 of the elongated element 140 may be omitted and the elongated element 140 may be directly driven by a motor.

Referring to FIGS. 5 to 9, another embodiment of a robotic instrument 132a is shown. Like components of the robotic instrument 132a bear like reference to their counterparts in the robotic instrument 132, except followed by the suffix "a". The robotic instrument 132a includes an end-effector assembly 136a, first and second elongated elements 140a and 180a respectively, and a drive assembly 144a.

Figure 5:
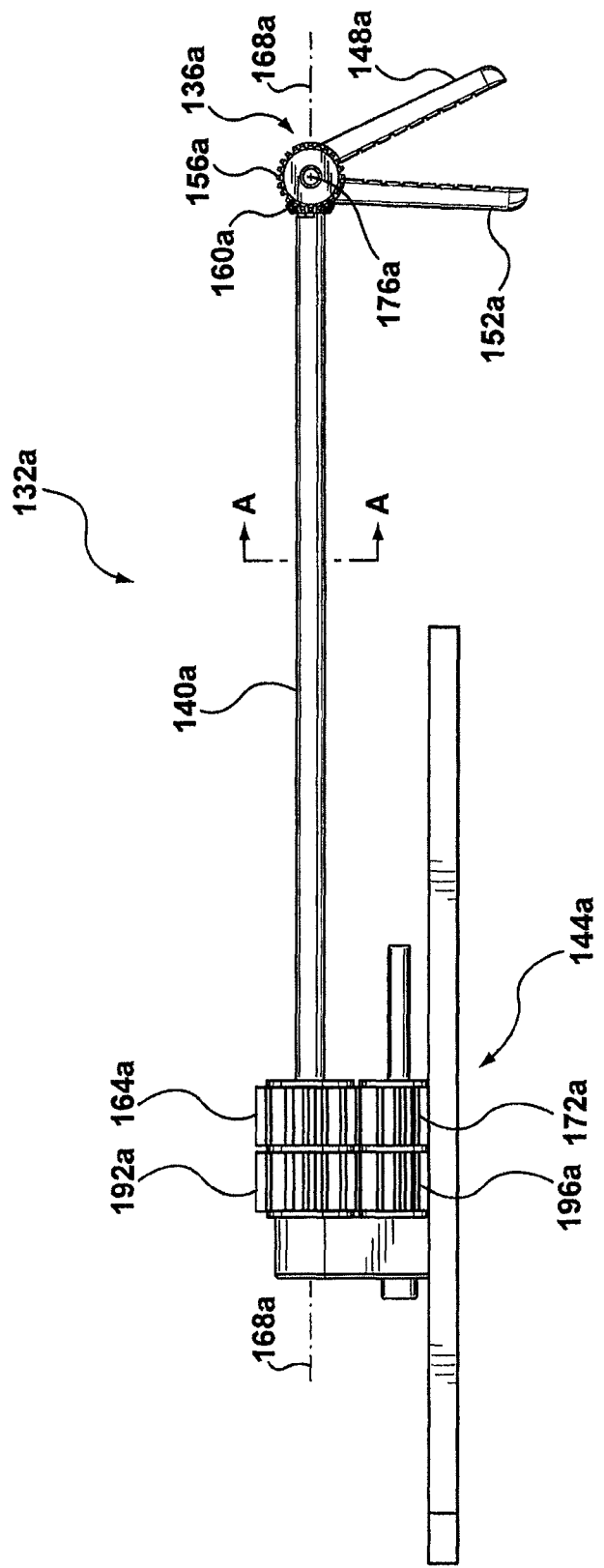
FIG. 5 is a perspective view of a robotic instrument in accordance with another embodiment.
Figure 6:
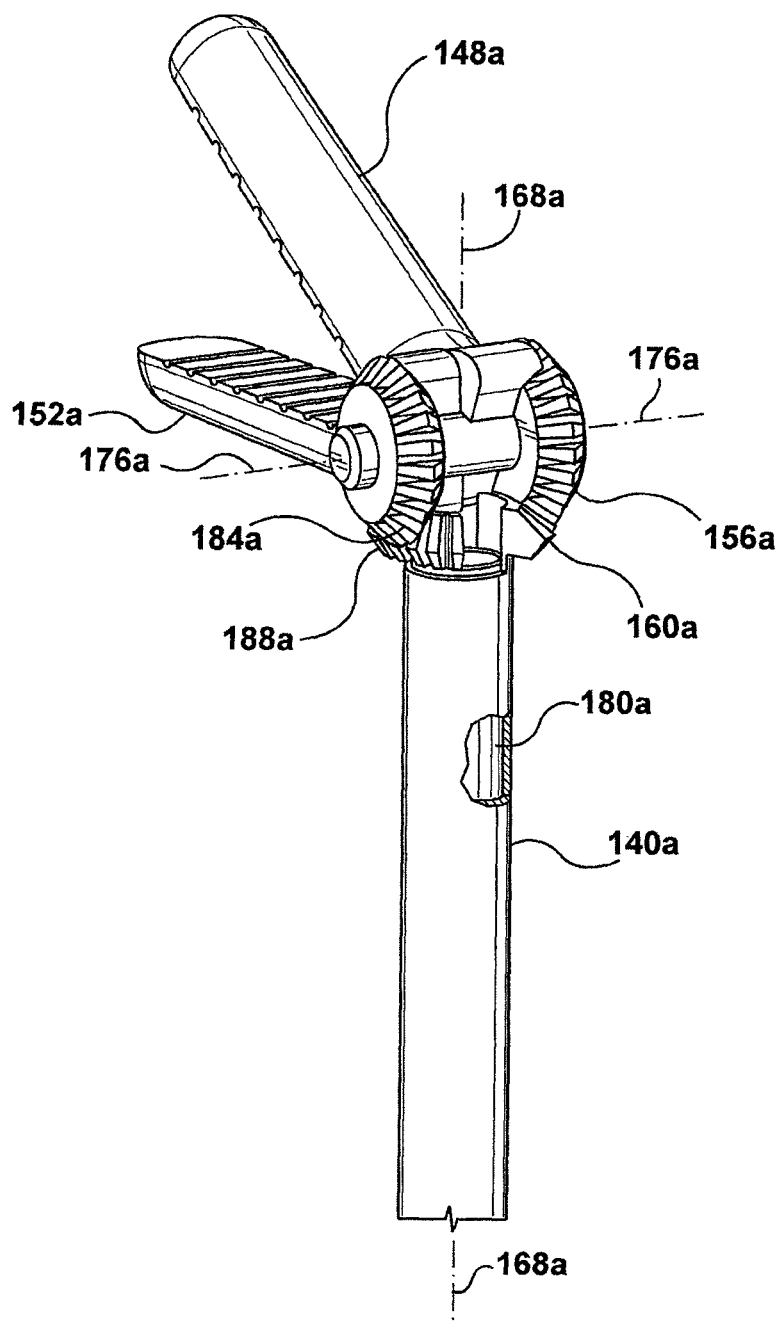
FIG. 6 is another perspective view of the robotic instrument in accordance with the embodiment of FIG. 5 with a cutaway portion.
Figure 7:
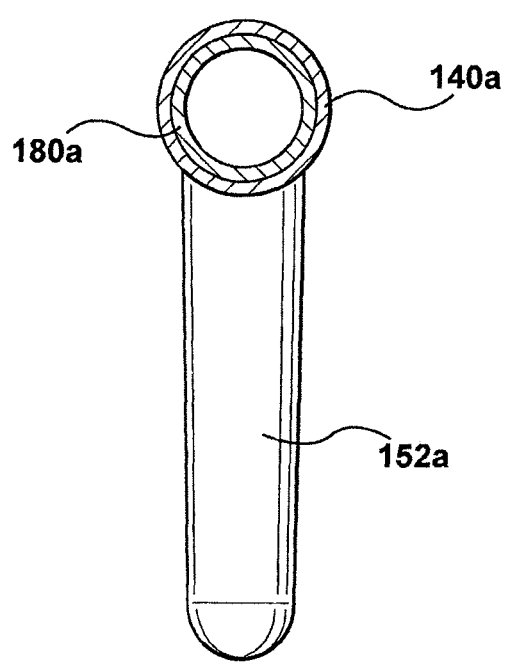
FIG. 7 is a cross sectional view of a robotic instrument in accordance with the embodiment of FIG. 5 through the line A-A.

In the present embodiment, the end-effector assembly 136a is shown in greater detail in FIG. 6. The end-effector assembly 136a is generally configured to interact with the patient P during MIS. The end-effector assembly 136a includes two working members 148a and 152a. The end-effector assembly 136a also includes two motion transfer mechanisms. In the present embodiment, the transfer mechanisms are first and second gears 156a and 184a each having a plurality of teeth. It is to be understood that the end-effector assembly 136a, including the working members 148a and 152a, is not particularly limited to any material and that several different types of materials are contemplated such as those contemplated for the end-effector assembly 136. The exact configuration of working members 148a and 152a is not particularly limited. In the present embodiment shown in FIGS. 5 to 9, the working members 148a and 152a are jaws of forceps. In other embodiments, the working members can be other surgical instruments such as scissors, blades, graspers, clip appliers, staplers, retractors, clamps or bi-polar cauterizers or combinations thereof. Also, in other embodiments the endeffector assembly may include a single working member such as imaging equipment, such as a camera or light source, or surgical instruments such as scalpels, hooks, needles, catheters, spatulas or mono-polar cauterizers.

Referring to FIG. 5, the first and second elongated elements 140a and 180a extend between the end-effector assembly 136a and the drive assembly 144a. The first and second elongated elements 140a and 180a are generally configured to support and control the end-effector assembly 136a. It is to be understood that the first and second elongated elements 140a and 180a are not particularly limited to any one type of material and that several different types of surgical-grade materials are contemplated such as those contemplated for the elongated element 140. The first and second elongated elements 140a and 180a each include two motion transfer mechanisms. In the present embodiment, the motion transfer mechanisms of the first elongated element 140a include first and second gears 160a and 164a each having a plurality of teeth and disposed at opposite ends of the elongated element 140a. The first gear 160a is configured to mate with the first gear 156a of the end-effector assembly 136a. The motion transfer mechanisms of the second elongated element 180a include first and second gears 188a and 192a each having a plurality of teeth and each disposed at opposite ends of the second elongated element 180a. The first gear 188a is configured to mate with the second gear 184a of the end-effector assembly 136a. In certain embodiments, the first and second elongated elements 140a and 180a are each rigid, such that independently applying a rotational torque about an axis 168a at the second gears 164a and 192a will cause the first and second elongated elements 14 0a and 180a, respectively, to rotate independently from each other without significant deformation. It will now be appreciated that the first gears 160a and 188a are configured to transfer rotational motion of the first and second elongated elements 140a and 180a to the first and second gears 156a and 184a of the end-effector assembly 136a to move, independently, the working members 148a and. 152a, respectively.

Referring to FIG. 6, the first gears 160a and 188a of the present embodiment are sector gears. Using sector gears in the present embodiment permits both of the first gears 160a and 188a to rotate within a range of angles in the same plane to independently control the working members 148a and 152a. It is to be understood that the first gears 160a and 188a are not limited to sector gears and that other embodiments are contemplated. For example, the first gears 160a and 188a can be modified to be other types of gears such as nested circular gear racks.

Figure 8:
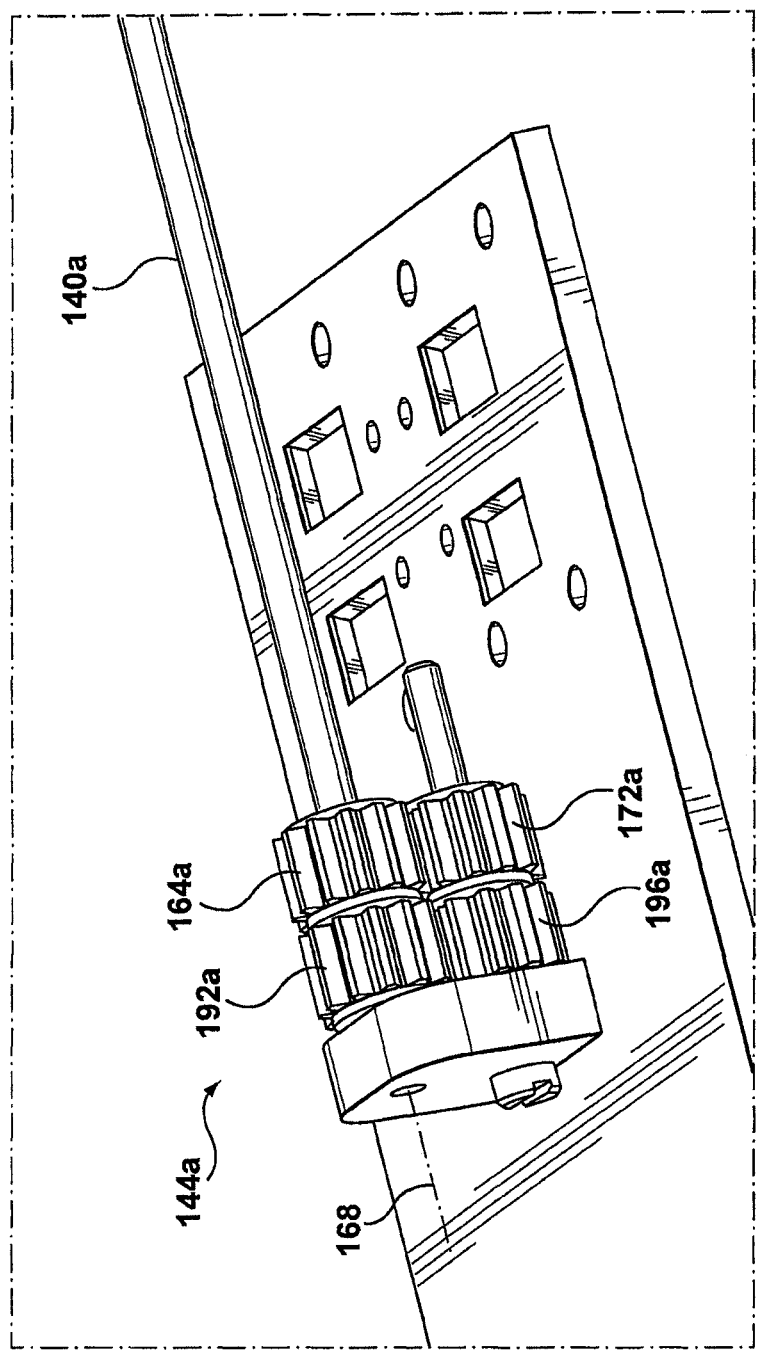
FIG. 8 is perspective view of a drive assembly of the robotic instrument in accordance with the embodiment of FIG. 5.

Referring to FIG. 8, the drive assembly 144a of the present embodiment is shown in greater detail in FIG. 8. The drive assembly 144 includes two motion transfer mechanisms. In the present embodiment, the transfer mechanisms are first and second drive gears 172a and 196a, each having a plurality of teeth. The first and second drive gears 172a and 196a are configured to mate with the gears 164a and 192a respectively. It will now be appreciated that the first and second drive gears 172a and 196a are configured to transfer, independently, motion from the drive assembly 144a to a rotational motion of the first and second elongated elements 140a and 180a about the axis 168a, respectively, by applying a rotational torque to the second gears 164a and 192a, respectively. The first and second drive gears 172a and 196a can be driven, independently, by various means, such as those discussed above in connection with drive assembly 144.

In operation, the present embodiment of the robotic instrument 132a controls the movement of the working members 148a and 152a of the end-effector assembly 136a. A source of motion in the drive assembly rotates the first and second drive gears 172a and 196a. The first and second drive gears 172a and 196a engage the second gears 164a and 192a of the elongated elements 140a and 180a, respectively. Therefore, as the drive gear 172a is rotated, engagement to second gear 164a of the first elongated element 140a will cause the first elongated element to rotate about the axis 168a. The rotation of the first elongated element 140a will cause a corresponding rotation of the first gear 160a. The first gear 160a engages the first gear 156a of the end-effector assembly 136a. Therefore, as the first gear 160a rotates, engagement to the first gear 156a of the end-effector assembly 136a will cause the working member 148a to pivot about a first axis 176a. Similarly, as the drive gear 196a is rotated, engagement to second gear 192a of the second elongated element 180a will cause the second elongated element to rotate about the axis 168a. The rotation of the second elongated element 180a will cause a corresponding rotation of the first gear 188a. The first gear 188a engages the second gear 184a of the end-effector assembly 136a. Therefore, as the first gear 188a rotates, engagement to the second gear 184a of the end-effector assembly 136a will cause the working member 152a to pivot about the first axis 176a.

It will now be appreciated by a person skilled in the art with the benefit of this description and the accompanying drawings that, in the present embodiment, the working members 148a and 152a can be pivoted about the first axis 176a independently to open and close the jaw.

Figure 9:
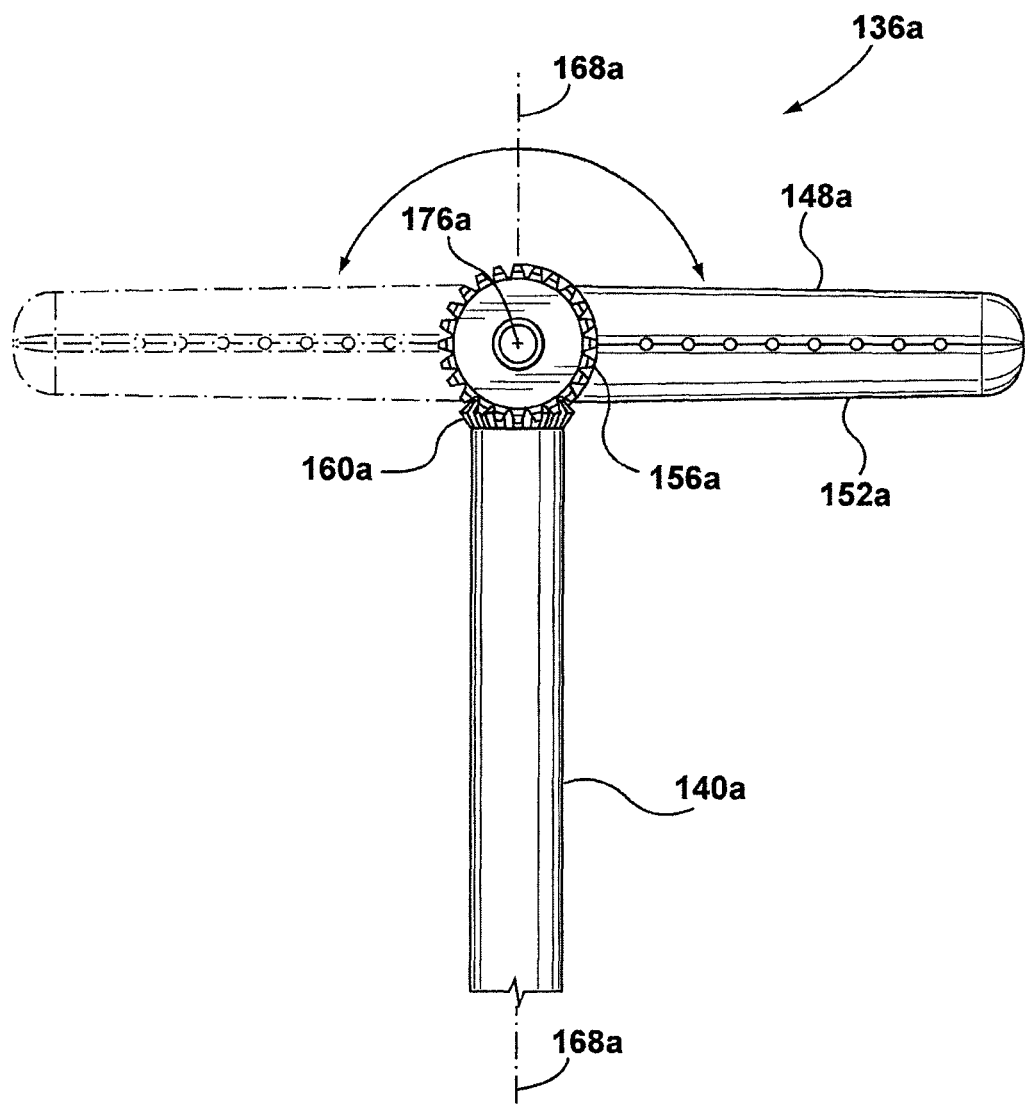
FIG. 9 is a view showing a movement of the robotic instrument of FIG. 5.

It will now be appreciated that the independent control of the working members 148a and 152a provides an addition degree of freedom over the robotic instrument 132 which involves rotating the working members 148a and 152a about the first axis 176a as shown in FIG. 9. Therefore, the independent control of the working members 148a and 152a allows the working members to open and close over a range of angles about the first axis 176a, whereas the working members 148 and 152 were only able to open can close at a fixed angle.

Variations are contemplated. For example, although the present embodiment shows the first and second elongated elements 140a and 180a are nested tubes, it is to be understood that the embodiment is purely exemplary and it will be apparent to those skilled in the art that a variety of different configurations of the first and second elongated elements 140a and 180a are contemplated. For example, the first elongated element 140a can be modified such that it is not a hollow tube. Furthermore, it is also contemplated that the second elongated element 180a can be modified into a solid rod in some embodiments. In other embodiments, the first and second elongated elements 140a and 180a, respectively, can be modified such that they are not nested and instead are parallel and adjacent.

Figure 10:
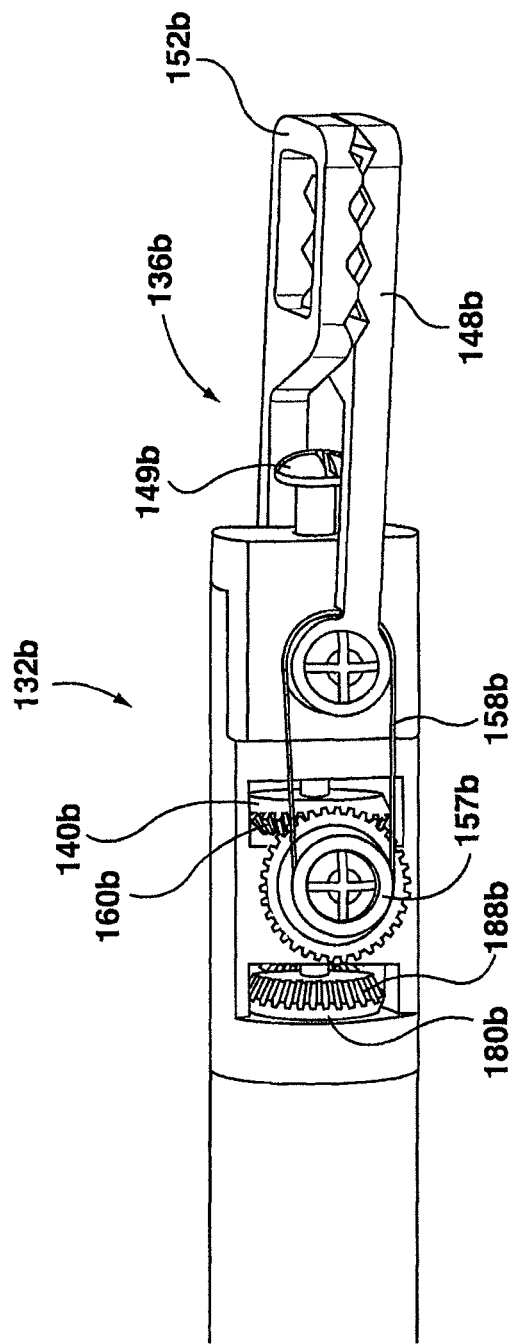
FIG. 10 is a perspective view of a robotic instrument in accordance with another embodiment.
Figure 11:
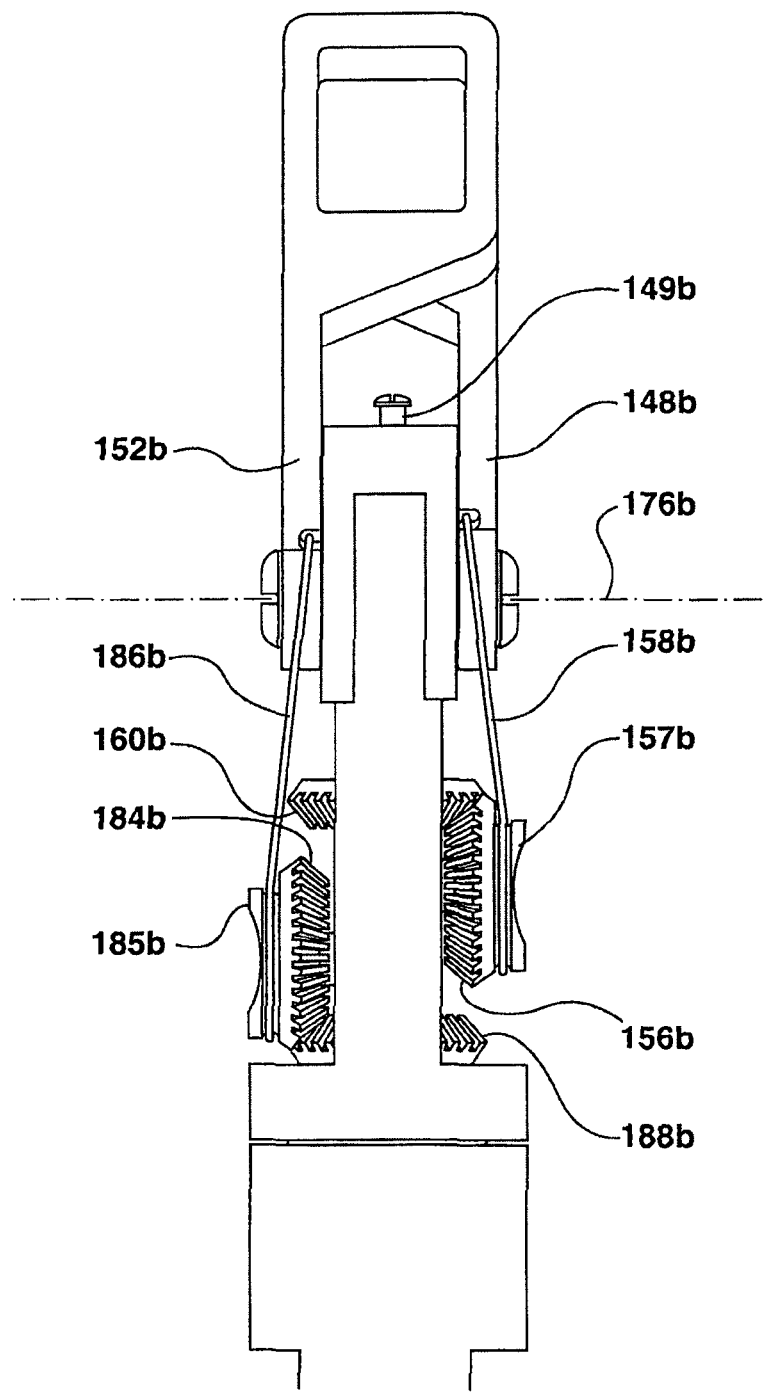
FIG. 11 is another perspective view of the robotic instrument in accordance with the embodiment of FIG. 10.

Referring to FIGS. 10 and 11, another embodiment of a robotic instrument 132b is shown. Like components of the robotic instrument 132b bear like reference to their counterparts in the robotic instruments 132 and 132a, except followed by the suffix "b". The robotic instrument 132b includes an end-effector assembly 136b, first and second elongated elements 140b and 180b respectively, and a drive assembly (not shown).

The end-effector assembly 136b is generally configured to interact with the patient P during MIS. The end-effector assembly 136b includes two working members 148b and 152b. The end-effector assembly 136b also includes two motion transfer mechanisms. In the present embodiment, the motion transfer mechanisms of the end-effector assembly 136b include a first rotating element 157b and a second rotating element 185b. A first gear 156b and a second gear 184b, each gear having a plurality of teeth, are disposed on the first and second rotating elements 157b and 185b, respectively. In the present embodiment, the motion transfer mechanisms further include a first end-effector cable 158b and a second end-effector cable 186b which are engaged with first and second rotating elements 157b and 185b (coupled to the first and second gears 156b and 184b, respectively) and the first and second working members 148b and 152b as shown in FIG. 11. In the present embodiment, the first end-effector cable 158b and a second end-effector cable 186b are cables suitable for surgical applications. In other embodiments, the first and second end-effector cables 158b and 186b can be modified to be a belt or chain. The end-effector assembly 136b also includes a set screw 149b configured to adjust the tension of the first and second end-effector cables 158b and 186b. Therefore, as the first and second end-effector cables 158b and 186b wear and expand over time, the set screw can be adjusted to maintain the required tension in the motion transfer mechanisms.

Referring to FIG. 10, the first and second elongated elements 140b and 180b extend between the end-effector assembly 136b and the drive assembly (not shown). The first and second elongated elements 140b and 180b are generally configured to support and control the end-effector assembly 136b. The first and second elongated elements 140b and 180b each include a motion transfer mechanism. In the present embodiment, the motion transfer mechanism of the first elongated element 140b includes a gear 160b having a plurality of teeth disposed thereon. The gear 160b is configured to mate with the first gear 156b on the first rotatable element 157b of the end-effector assembly 136b. The motion transfer mechanism of the second elongated element 180b includes a gear 188b having a plurality of teeth 180b disposed thereon. The gear 188b is configured to mate with the second gear 184b on the second rotatable element 185b of the end-effector assembly 136b. It will now be appreciated that the gears 160b and 188b are configured to transfer rotational motion of the first and second elongated elements 140b and 180b to the first and second gears 156b and 184b to move, independently, the first and second rotatable elements 157b and 185b, respectively. In turn the first and second rotatable elements 157b and 185b apply tension to the first and second endeffector cables 158b and 185b to move the working members 148b and 152b, respectively.

It will now be appreciated by a person skilled in the art with the benefit of this description and the accompanying drawings that, in the present embodiment, the working members 148b and 152b can be pivoted about the first axis 176b (shown in FIG. 11) independently to open and close the jaw. Furthermore, it will also now be appreciated that by using first and second rotatable elements 157b and 185b in combination with the first and second end-effector cables 158b and 186b, the range of motion of the first and second working members 148*b* and 152*b* is increased compared with the embodiment shown in FIG. 6 where the gears 160*a* and 188*a* are sector gears.

Referring to FIGS. 12 to 16, another embodiment of a robotic instrument 132*c* is shown. Like components of the robotic instrument 132*c* bear like reference to their counterparts in the robotic arms 132 and 132*a*, except followed by the suffix "c". The robotic instrument 132*c* includes an end-effector assembly 136*c*, first, second, and third elongated elements 140*c*, 180*c*, and 200*c* respectively, and a drive assembly 144*c*.

Figure 12:
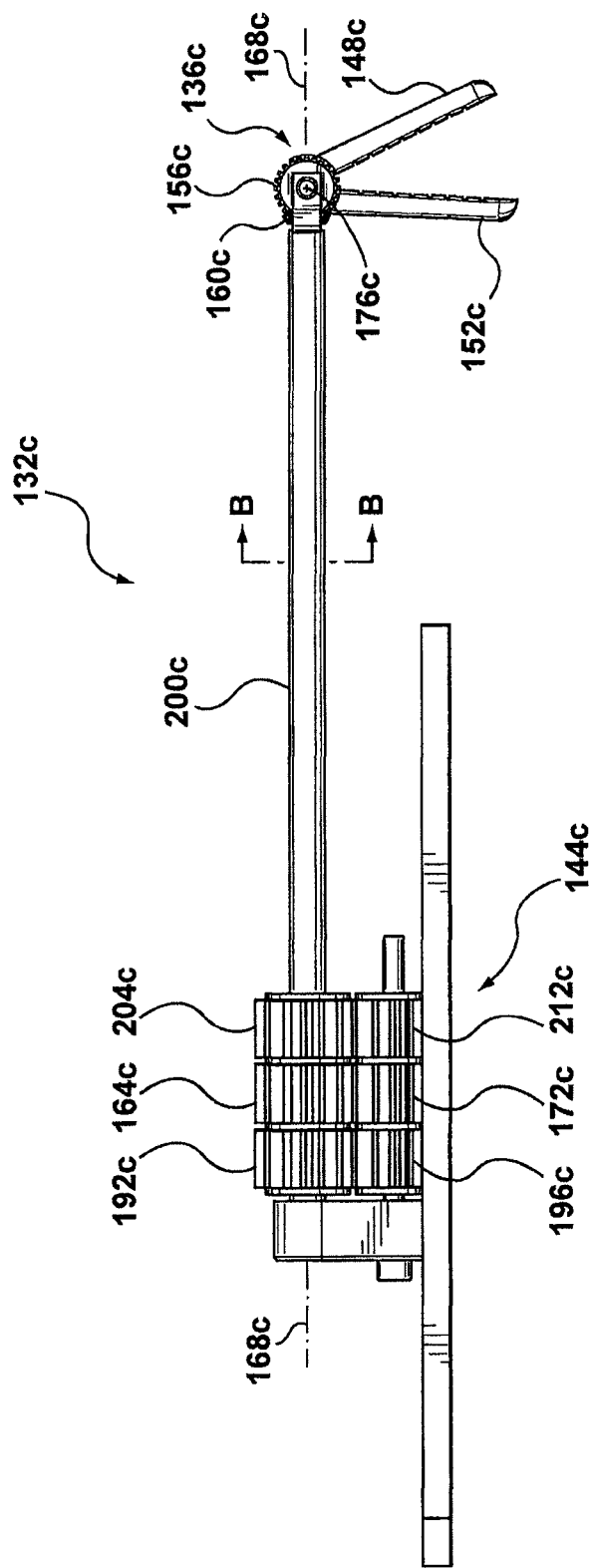
FIG. 12 is a perspective view of a robotic instrument in accordance with another embodiment.
Figure 13:
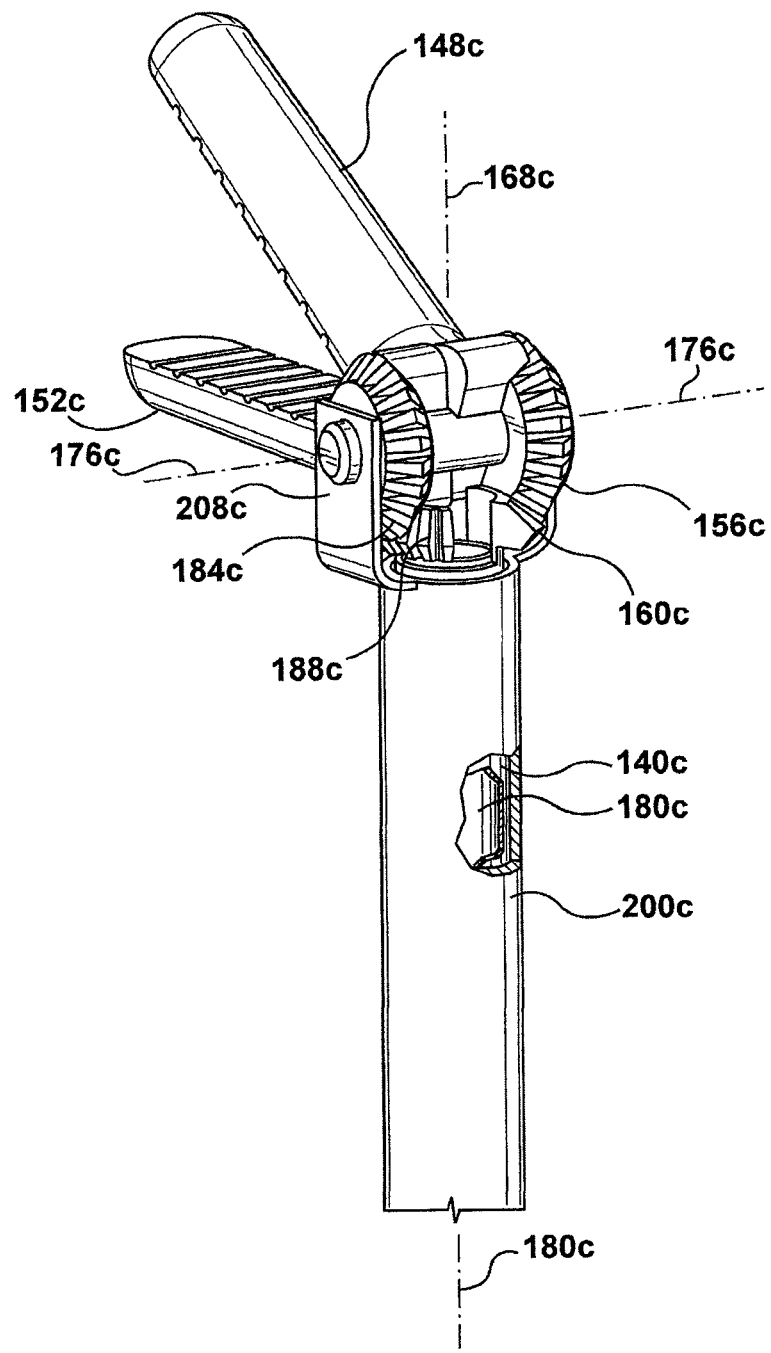
FIG. 13 is another perspective view of the robotic instrument in accordance with the embodiment of FIG. 12 with a cutaway portion.

In the present embodiment, the end-effector assembly 136*c* is shown in greater detail in FIG. 13. The end-effector assembly 136*c* is generally configured to interact with the patient P during MIS. The end-effector assembly 136*c* includes two working members 148*c* and 152*c*. The end-effector assembly 136*c* also includes two motion transfer mechanisms. In the present embodiment, the transfer mechanisms are first and second gears 156*c* and 184*c* each having a plurality of teeth. It is to be understood that the end-effector assembly 136*c*, including the working members 148*c* and 152*c*, is not particularly limited to any material and that several different types of materials are contemplated such as those contemplated for the end-effector assemblies 136 and 136*a*. The exact configuration of working members 148*c* and 152*c* is not particularly limited. In the present embodiment shown in FIGS. 12 to 16, the working members 148*c* and 152*c* are jaws of forceps.

Referring to FIGS. 12 and 13, the first, second, and third elongated elements 140*c*, 180*c*, and 200*c* extend between the end-effector assembly 136*c* and the drive assembly 144*c*. The first, second, and third elongated elements 140*c*, 180*c*, and 200*c* are generally configured to support and control the end-effector assembly 136*c*. It is to be understood that the first, second, and third elongated elements 140*c*, 180*c*, and 200*c* are not particularly limited to any one type of material and that several different types of surgical-grade materials are contemplated such as those contemplated for the elongated elements 140, 140*a* and 180*a*. The first and second elongated elements 140*c* and 180*c* each include two motion transfer mechanisms. In the present embodiment, the motion transfer mechanisms of the first elongated element 140*c* include first and second gears 160*c* and 164*c* each having a plurality of teeth and disposed at opposite ends of the elongated element 140*c*. The first gear 160*c* is configured to mate with the first gear 156*c* of the end-effector assembly 136*c*. The motion transfer mechanisms of the second elongated element 180*c* include first and second gears 188*c* and 192*c* each having a plurality of teeth and each disposed at opposite ends of the second elongated element 180*c*. The first gear 188*c* is configured to mate with the second gear 184*c* of the end-effector assembly 136*c*. The third elongated element 200*c* includes a motion transfer mechanism. In the present embodiment, the motion transfer mechanism of the third elongated element 200*c* is a gear 204*c* disposed the end of the third elongated element 200*c* proximate to the drive assembly 144*c*. The opposite end 208*c* of the third elongated element 200*c* is connected to the end-effector assembly 136*c*.

In certain embodiments, the first, second, and third elongated elements 140*c*, 180*c*, and 200*c* are each rigid, such that independently applying a rotational torque about an axis 168*c* at the gears 164*c*, 192*c*, and 204*c* will cause the first, second, and third elongated elements 140*c*, 180*c*, and 200*c*, respectively, to rotate independently from each other without significant deformation. It will now be appreciated that the first gears 160*c* and 188*c* of the first and second elongated elements 140*c* and 180*c* are configured to transfer rotational motion of the first and second elongated elements to the first and second gears 156*c* and 184*c* of the endeffector assembly 136*c* to move, independently, the working members 148*c* and 152*c*, all respectively.

Figure 15:
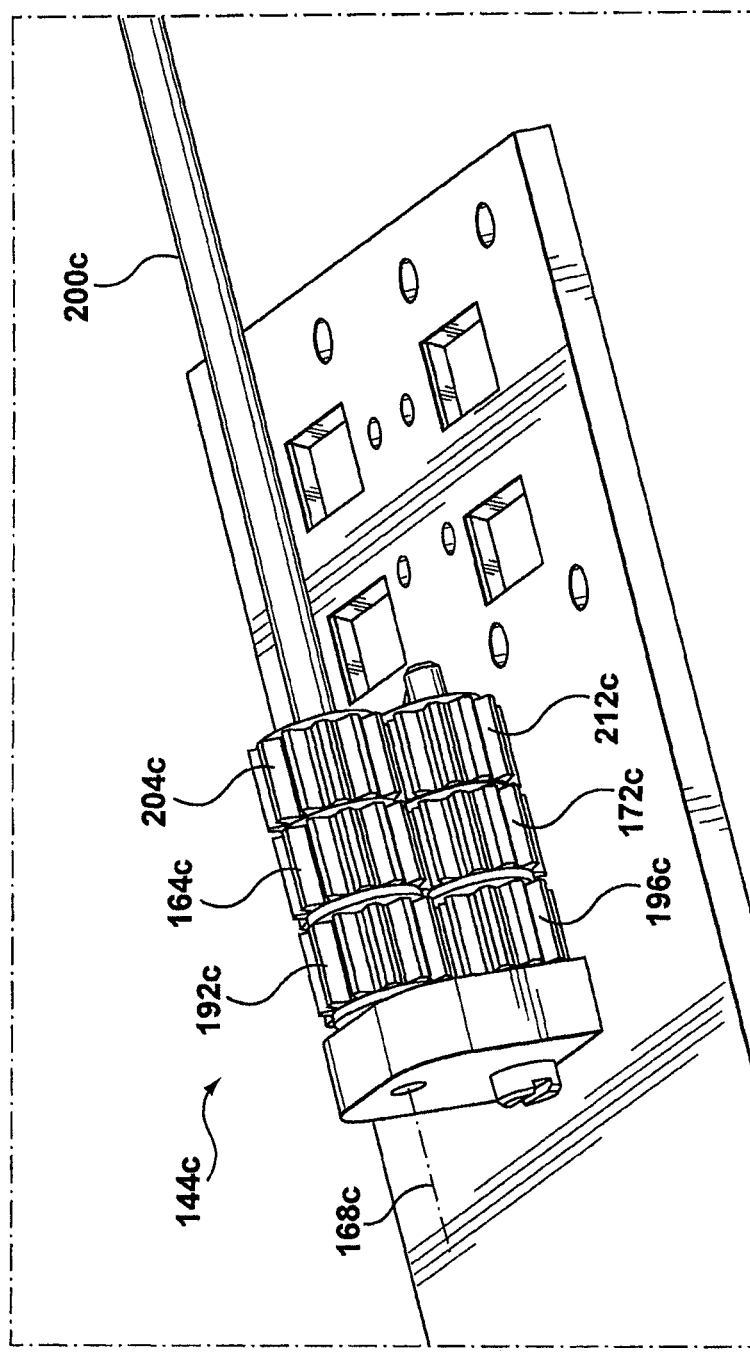
FIG. 15 is perspective view of a drive assembly of the robotic instrument in accordance with the embodiment of FIG. 12.

Referring to FIG. 15, the drive assembly 144*c* of the present embodiment is shown in greater detail in FIG. 15. The drive assembly 144*c* includes three motion transfer mechanisms. In the present embodiment, the transfer mechanisms are first, second, and third drive gears 172*c*, 196*c*, and 212*c* each having a plurality of teeth. The first, second, and third drive gears 172*c*, 196*c*, and 212*c* are configured to mate with the gears 164*c*, 192*c*, and 204*c* respectively. It will now be appreciated that the first, second, and third drive gears 172*c*, 196*c*, and 212*c* are configured to transfer, independently, motion from the drive assembly 144*c* to a rotational motion of the first, second, and third elongated elements 140*c*, 180*c*, and 200*c* about the axis 168*c*, respectively, by applying a rotational torque to the gears 164*c*, 192*c*, and 204*c*, respectively. The first, second, and third drive gears 172*c*, 196*c*, and 212*c* can be driven, independently, by various means, such as those discussed above in connection with drive assemblies 144 and 144*a*.

In operation, the present embodiment of the robotic instrument 132*c* controls the movement of the end-effector assembly 136*c*, which includes the movements of the working members 148*c* and 152*c*. A source of motion in the drive assembly 144*c* rotates the first, second, and third drive gears 172*c*, 196*c*, and 212*c*. The first, second, and third drive gears 172*c*, 196*c*, and 212*c* engage the gears 164*c*, 192*c*, and 204*c* of the first, second and third elongated elements 140*c*, 180*c*, and 200*c* respectively. Therefore, as the drive gear 172*c* is rotated, engagement to second gear 164*c* of the first elongated element 140*c* will cause the first elongated element to rotate about the axis 168*c*. The rotation of the first elongated element 140*c* will cause a corresponding rotation of the first gear 160*c*. The first gear 160*c* engages the first gear 156*c* of the end-effector assembly 136*c*. Therefore, as the first gear 160*c* rotates, engagement to the first gear 156*c* of the end-effector assembly 136*c* will cause the working member 148*c* to pivot about a first axis 176*c*. Similarly, as the drive gear 196*c* is rotated, engagement to second gear 192*c* of the second elongated element 180*c* will cause the second elongated element to rotate about the axis 168*c*. The rotation of the second elongated element 180*c* will cause a corresponding rotation of the first gear 188*c*. The first gear 188*c* engages the second gear 184*c* of the end-effector assembly 136*c*. Therefore, as the first gear 188*c* rotates, engagement to the second gear 184*c* of the end-effector assembly 136*c* will cause the working member 152*c* to pivot about the first axis 176*c*. As the drive gear 212*c* is rotated, engagement to gear 204*c* of the third elongated element 200*c* will cause the third elongated element to rotate about the axis 168*c*. The rotation of the third elongated element 200*c* will cause a corresponding rotation of the end 208*c*. Since the end 208*c* is connected to the end-effector assembly 136*c*, rotation of the third elongated element 200*c* will cause the end-effector assembly 136*c* to rotate about the axis 168*c*. It will now be appreciated by a person skilled in the art with the benefit of this description and the accompanying drawings that, in the present embodiment, the working members 148*c* and 152*c* can be pivoted about the first axis 176*c* independently to open and close the jaw. It will also now be appreciated that since the end-effector assembly 136*c* can be rotated about the axis 168*c*, the first axis 176*c* is not necessarily fixed and can be rotated as well.

Figure 14:
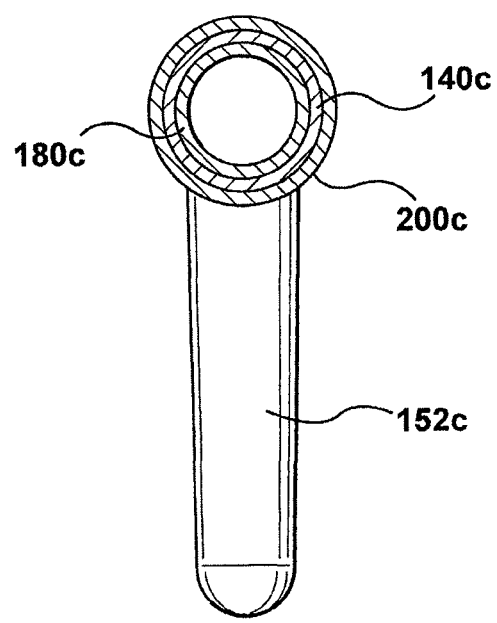
FIG. 14 is a cross sectional view of a robotic instrument in accordance with the embodiment of FIG. 12 through the line B-B.
Figure 16:
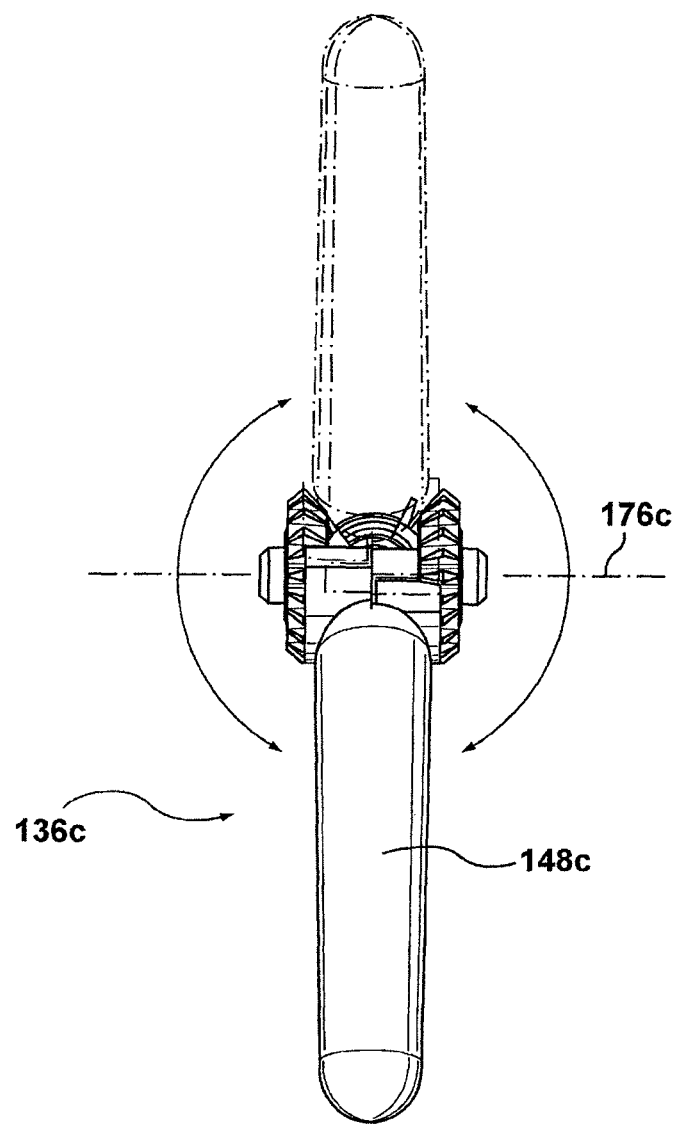
FIG. 16 is a view showing a movement of the robotic instrument of FIG. 12.

Referring to FIG. 16, it will now be appreciated that the independent rotation of the end-effector assembly 136c provides an addition degree of freedom over the robotic instrument 132a which involves rotating the working members 148c and 152c about the axis 168c as shown in FIG. 16, where the axis 168c is shown in FIGS. 12, 14, and 15. Therefore, independent control of the third elongated element 200c allows the working members 148c and 152c to reach over all angles about the axis 168c. This specific degree of freedom is referred to as a roll motion. It is to be understood that variations are contemplated whereby the axis 168c is not straight, such as the embodiment generally shown in FIG. 24, which will be discussed later as an embodiment where the elongated element can be bent.

Variations are contemplated. For example, although the present embodiment shows the first, second, and third elongated elements 140c, 180c, and 200c are nested tubes, it is to be understood that the embodiment is purely exemplary and it will be apparent to those skilled in the art that a variety of different configurations of the first, second, and third elongated elements 140c, 180c, and 200c are contemplated. In other embodiments, the first, second, and third elongated elements 140c, 180c, and 200c, respectively, can be modified such that they are not nested and instead are parallel and adjacent.

Figure 17:
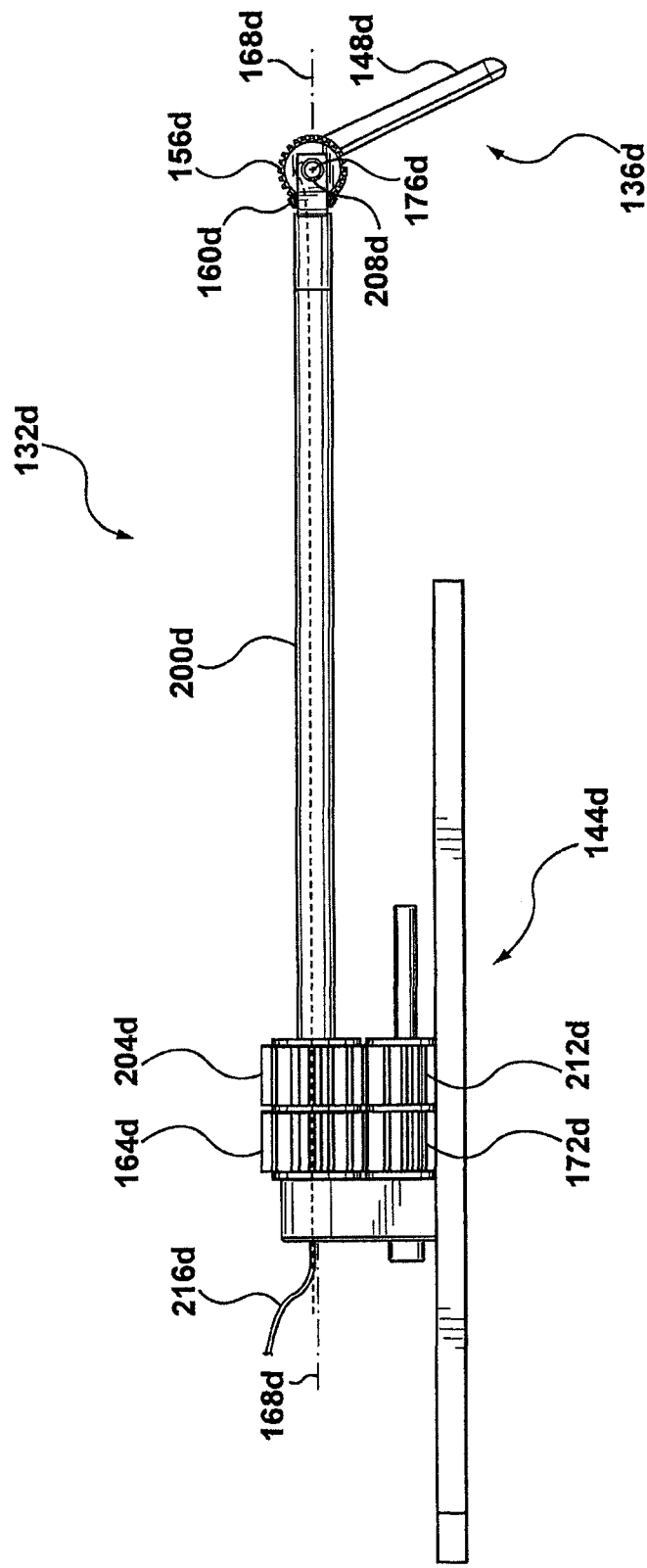
FIG. 17 is a perspective view of a robotic instrument in accordance with another embodiment.
Figure 18:
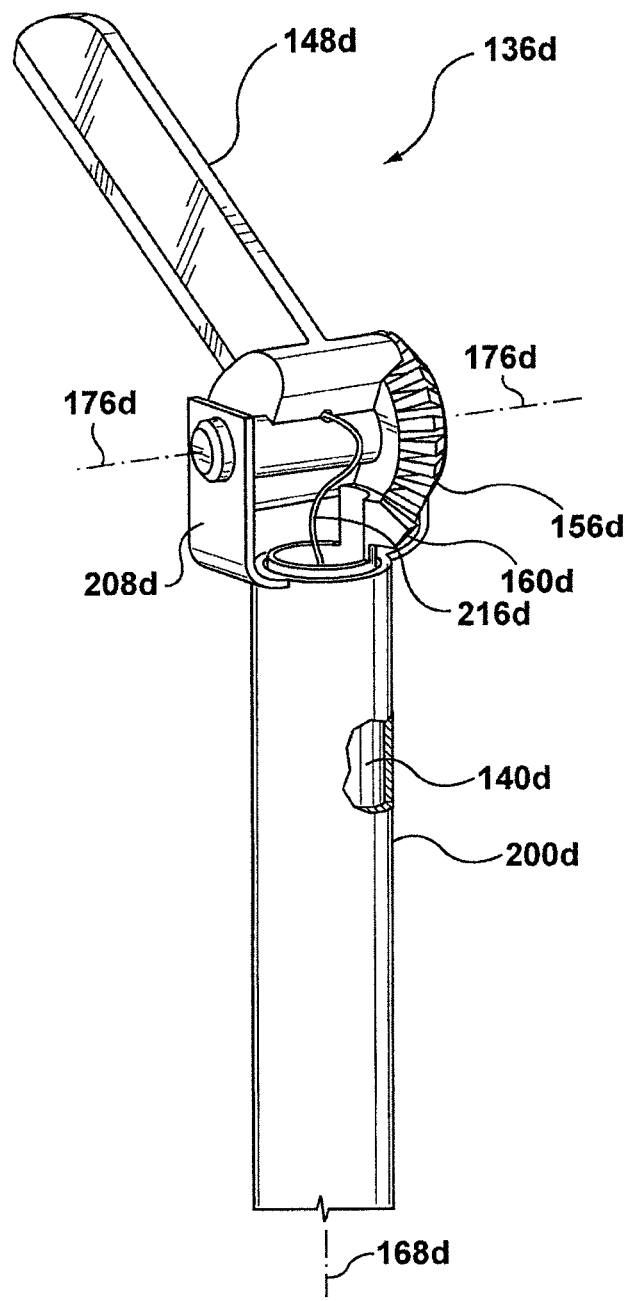
FIG. 18 is another perspective view of the robotic instrument in accordance with the embodiment of FIG. 17 with a cutaway portion.

Referring to FIGS. 17 and 18, another embodiment of a robotic instrument 132d is shown. Like components of the robotic instrument 132d bear like reference to their counterparts in the robotic arms 132, 132a and 132d, except followed by the suffix "d". The robotic instrument 132d includes an end-effector assembly 136d, first and second elongated elements 140d and 200d respectively, and a drive assembly 144d.

In the present embodiment, the end-effector assembly 136d is shown in greater detail in FIG. 18. The end-effector assembly 136d is generally configured to interact with the patient P during MIS. The end-effector assembly 136d includes a working member 148d. The end-effector assembly 136d also includes a motion transfer mechanism. In the present embodiment, the transfer mechanism is a gear 156d having a plurality of teeth. It is to be understood that the end-effector assembly 136d, including the working member 148d, is not particularly limited to any material and that several different types of materials are contemplated such as those contemplated for the end-effector assemblies 136, 136a, and 136c. The exact configuration of the working member 148d is not particularly limited. In the present embodiment shown in FIGS. 17 and 18, the working member 148d is a surgical blade capable of cauterizing.

Referring again to FIGS. 17 and 18, the first and second elongated elements 140d and 200d extend between the end-effector assembly 136d and the drive assembly 144d. The first and second elongated elements 140d and 200d are generally configured to support and control the end-effector assembly 136d. It is to be understood that the first and second elongated elements 140d and 200d are not particularly limited to any one type of material and that several different types of surgical-grade materials are contemplated. The first elongated element 140d includes two motion transfer mechanisms. In the present embodiment, the motion transfer mechanisms of the first elongated element 140d include first and second gears 160d and 164d each having a plurality of teeth and disposed at opposite ends of the elongated element 140d. The first gear 160d is configured to mate with the gear 156d of the end-effector assembly 136d. The second elongated element 200d includes a motion transfer mechanism. In the present embodiment, the motion transfer mechanism of the second elongated element 200d is a gear 204d disposed the end of the second elongated element 200d proximate to the drive assembly 144d. The opposite end 208d of the second elongated element 200d is connected to the end-effector assembly 136d.

In the present embodiment, the robotic instrument 132d additionally includes an electrical wire 216d extending through the first elongated element 140d to the working member 148d. The electrical wire 216d is generally configured to supply an electrical current to the working member 148d. The electrical current can be used to generate heat at the working member 148d to cauterize tissue when necessary. Although the present embodiment uses the electrical wire 216d, the robotic instrument can modified to provide the same functionality without an electrical wire. For example, the first elongated element 140d can be made of stainless steel, which is electrically conductive. Therefore, the electrical conductivity of the first elongated element 140d can be used in place of the electrical wire 216d.

In certain embodiments, the first and second elongated elements 140d and 200d are each rigid, such that independently applying a rotational torque about an axis 168d at the gears 164d and 204d will cause the first and second elongated elements 140d and 200d, respectively, to rotate independently from each other without significant deformation. It will now be appreciated that the first gear 160d of the first elongated elements 140d is configured to transfer rotational motion of the first elongated element 140d to the gear 156d of the end-effector assembly 136d to move the working member 148d.

Referring again to FIGS. 17 and 18, the drive assembly 144d includes two motion transfer mechanisms. In the present embodiment, the transfer mechanisms are first and second drive gears 172d and 212d, each having a plurality of teeth. The first and second drive gears 172d and 212d are configured to mate with the gears 164d and 204d respectively. It will now be appreciated that the first and second drive gears 172a and 212d are configured to transfer, independently, motion from the drive assembly 144d to a rotational motion of the first and second elongated elements 140d and 200d about the axis 168d, respectively, by applying a rotational torque to the second gears 164d and 204d, respectively. The first and second drive gears 172d and 212d can be driven, independently, by various means, such as those discussed above in connection with drive assemblies 144, 144a, and 144d.

In operation, the present embodiment of the robotic instrument 132d controls the movement of the end-effector assembly 136d, which includes the movements of the working member 148d. A source of motion in the drive assembly 144d rotates the first and second drive gears 172d and 212d. The first and second drive gears 172d and 212d engage the gears 164d and 204d of the first and second elongated elements 140d and 200d respectively. Therefore, as the drive gear 172d is rotated, engagement to gear 164d of the first elongated element 140d will cause the first elongated element to rotate about the axis 168d. The rotation of the first elongated element 140d will cause a corresponding rotation of the first gear 160d. The gear 160d engages the gear 156d of the end-effector assembly 136d. Therefore, as the gear 160d rotates, engagement to the gear 156d of the end-effector assembly 136d will cause the working member 148d to pivot about a first axis 176d. Similarly, as the drive gear 212d is rotated, engagement to gear 204d of the second elongated element 200d will cause the second elongated element to rotate about the axis 168d. The rotation of the second elongated element 200d will cause a corresponding rotation of the end 208d. Since the end 208d is connected to the end-effector assembly 136d, rotation of the second elongated element 200d will cause the end-effector assembly 136d to rotate about the axis 168d. It will now be appreciated by a person skilled in the art with the benefit of this description and the accompanying drawings that, in the present embodiment, the working member 148d can be pivoted about the first axis 176d independently from the rotation of the end-effector assembly 136d.

Variations are contemplated. For example, although the present embodiment shows a single working member 148d, the robotic instrument 132d can be modified to include a different number of working members. For example, previous embodiments show variations including two working members. However, the number of working members are not limited to two and a larger number of working members are contemplated.

Figure 19:
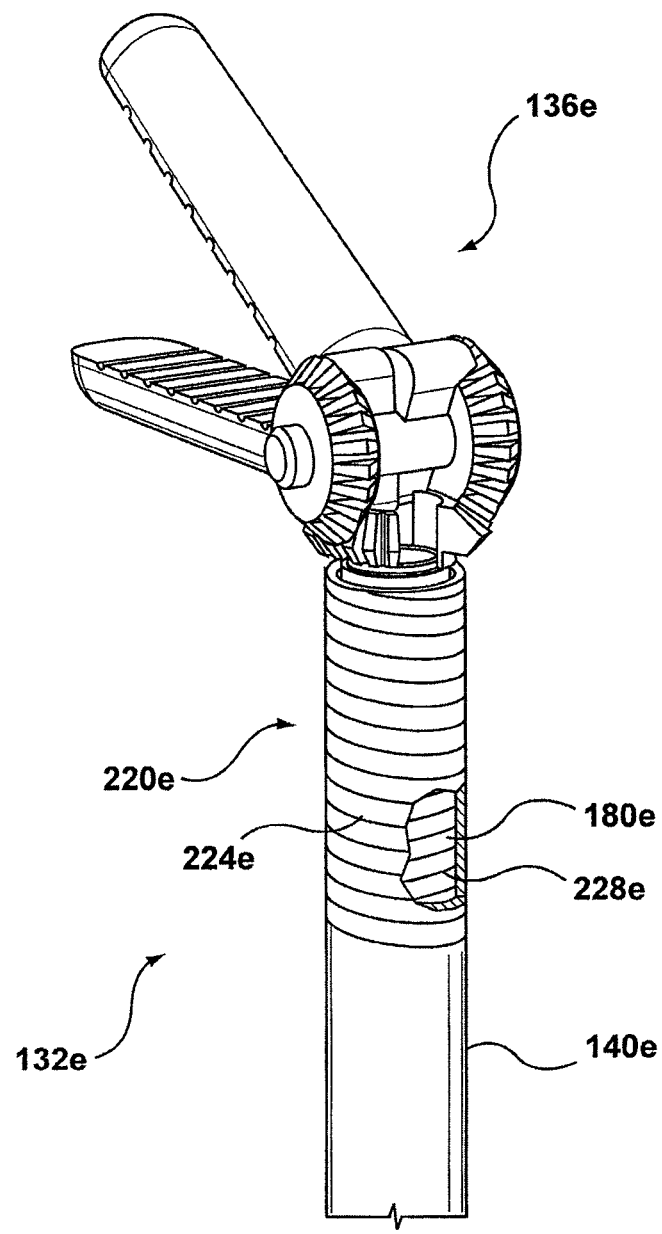
FIG. 19 is a perspective view of a robotic instrument in accordance with another embodiment.

Referring to FIG. 19, another embodiment of a robotic instrument 132e is shown. Like components of the robotic instrument 132e bear like reference to their counterparts, except followed by the suffix "e". The robotic instrument 132e includes an end-effector assembly 136e, first and second elongated elements 140e and 180e respectively, and a drive assembly (not shown).

Each elongated element 140e and 180e include a flexible portion disposed generally at 220e. The flexible portion allows for coarse motion of the elongated elements 140e and 180e, which provides even more degrees of freedom to the robotic instrument 132e. The flexible portion can be provided by using laser cutting techniques on the first and second elongated elements 140e and 180. The first and second laser cut elongated elements 140e and 180 may be obtained from Pulse Systems (Concord, California, U.S.A.) using uncut stainless steel tubes from Vita Needle (Needham, Massachusetts, U.S.A.). By laser cutting a stainless steel tube, it has been found that the flexibility of the stainless steel tube dramatically increases without compromising the rotational rigidity. Therefore, the laser cut stainless steel tubes have been shown to work well for providing flexibility, while still being effective at transferring rotational motion from a drive assembly to the end-effector assembly 136e. Although the laser cutting is shown in FIG. 19 to have produced spiral scores 224e and 228e on the first and second elongated elements 140e and 180e, respectively, variations are contemplated. It will now be appreciated that different laser cut patterns can have different characteristics and that the cut pattern selected depends on various factors.

It is also contemplated that other ways of providing a flexible portion can be used. For example, the composition of the elongated elements 140e and 180e can be varied such that a portion of each elongated element 140e and 180e is more flexible than other portions.

Figure 20:
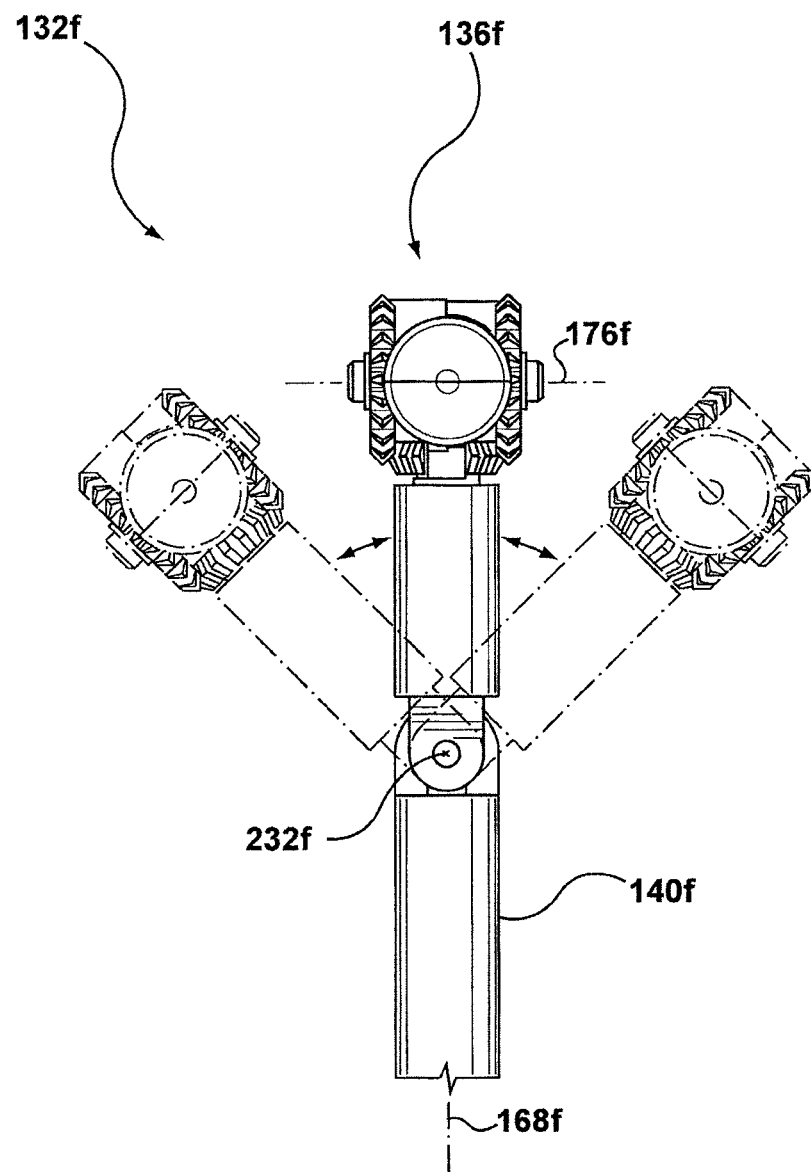
FIG. 20 is a perspective view showing a movement of a robotic instrument in accordance with another embodiment.
Figure 21:
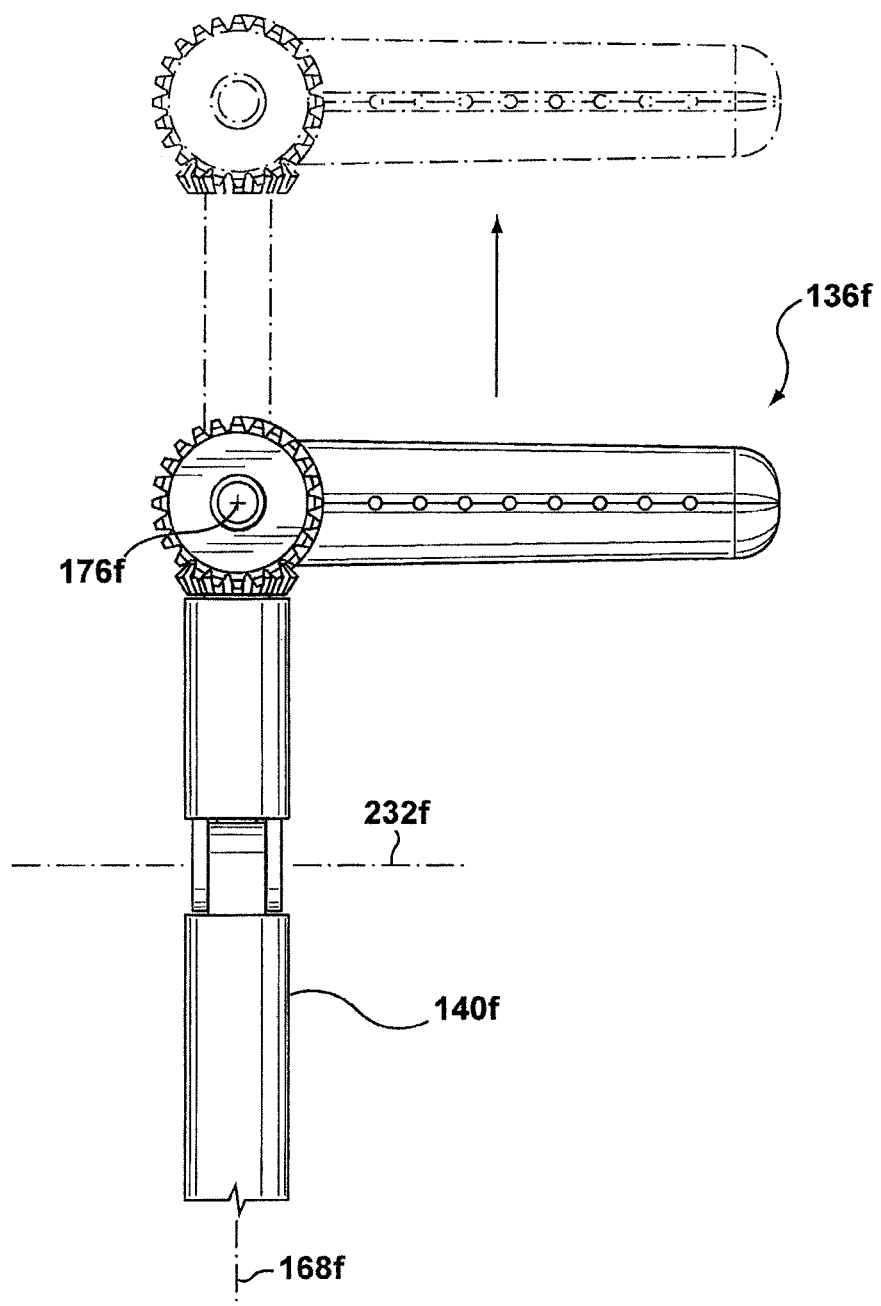
FIG. 21 is a perspective view showing the another movement of a robotic instrument in accordance with the embodiment of FIG. 20.

FIGS. 20 and 21 provide view of another exemplary robotic instrument 132f and its associated end-effector assembly 136f The robotic instrument 132f includes an end-effector assembly 136f and an elongated element 140f The end-effector assembly 136f is configured for another degree of freedom. The rotational motion shown in FIG. 20 is a degree of freedom which involves rotating the end-effector assembly 136f about the second axis 232f In some embodiments, the second axis 232f is perpendicular to the first axis 176f to provide the robotic instrument 132f with the greatest range of motion. However, it is not essential that the second axis 232f be perpendicular to the first axis 176f For example, similar to some of the previously discussed embodiments, the first axis 176f can be rotatable relative to the second axis 232f.

FIG. 21 shows another degree of freedom involving a longitudinal translation motion allowing the robotic instrument 132f to be translated along axis 168f For example, this allows the robotic instrument 132f to enter and penetrate deeper into the body, or be retracted. Unlike the other degrees of freedom discussed, this translational degree of freedom is provided by a system on the robotic arm 128. For example, the robotic arm can include a z-rail system (not shown) for moving the entire robotic instrument 132f.

Figure 22:
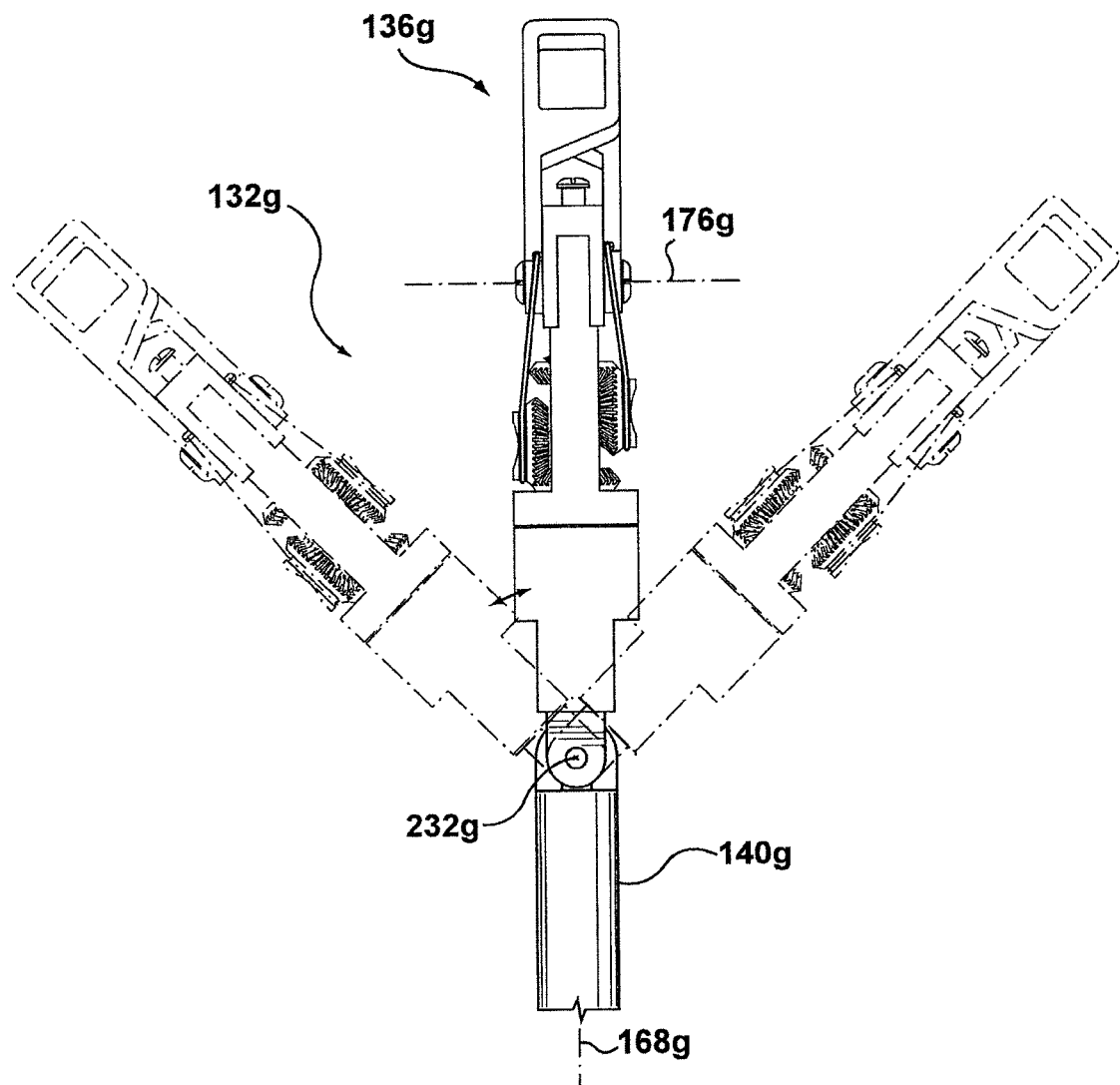
FIG. 22 is a perspective view showing a movement of a robotic instrument in accordance with another embodiment.
Figure 23:
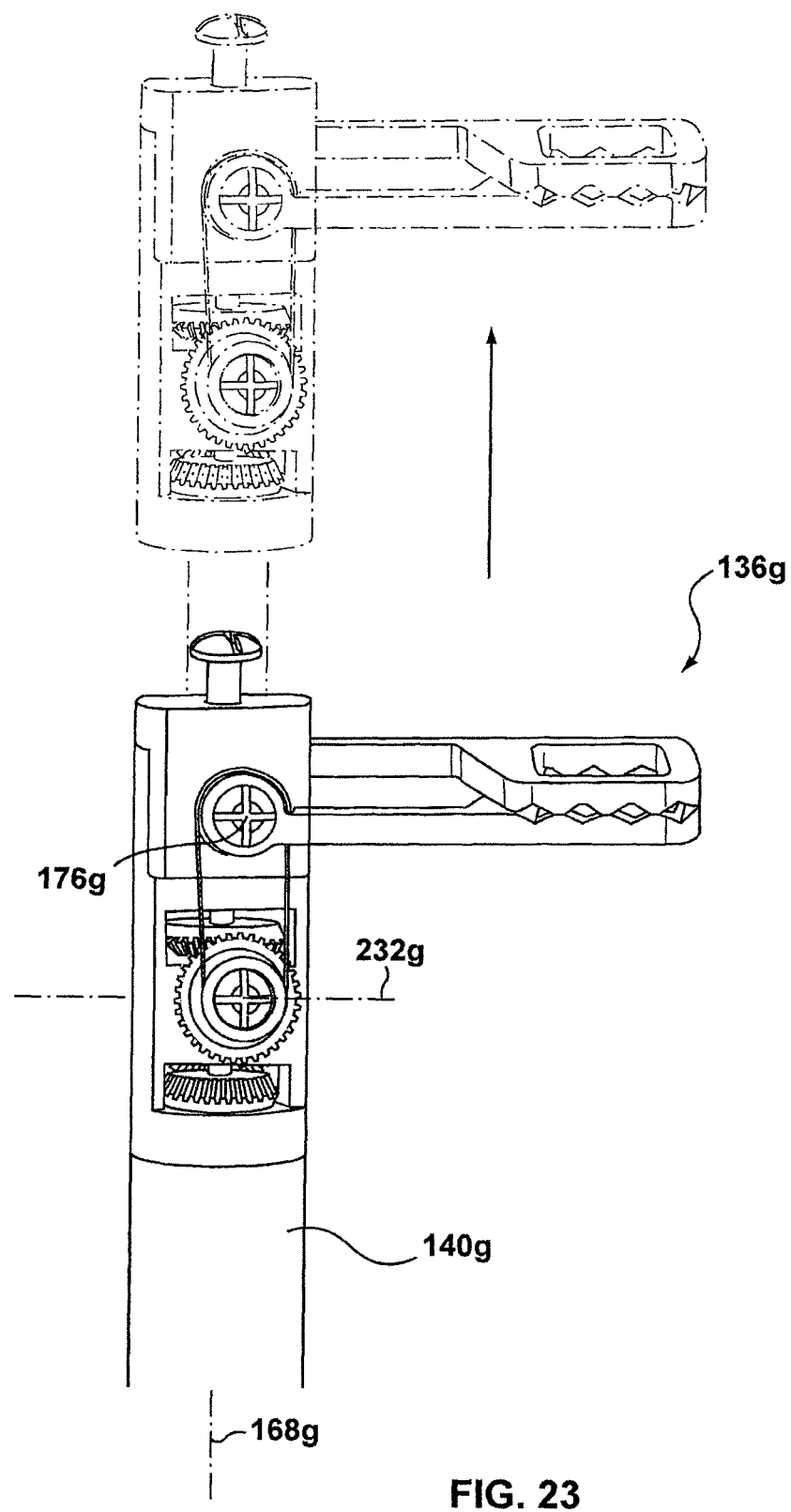
FIG. 23 is a perspective view showing the another movement of a robotic instrument in accordance with the embodiment of FIG. 22.

FIGS. 22 and 23 provide view of another exemplary robotic instrument 132g and its associated end-effector assembly 136g. The robotic instrument 132g includes an end-effector assembly 136g and an elongated element 140g. The end-effector assembly 136g is configured for another degree of freedom similar to the end-effector assembly 136f.

FIG. 23 shows another degree of freedom involving a longitudinal translation motion allowing the robotic instrument 132g to be translated along axis 168g. For example, this allows the robotic instrument 132g to enter and penetrate deeper into the body, or be retracted. For example, the robotic arm can include a z-rail system (not shown) for moving the entire robotic instrument 132g.

It is to be understood that degrees of freedom allow for a range of movements for facilitating MIS. Variations are contemplated and additional degrees of freedom not discussed in this application can be added. For example, the robotic instrument 132f can be externally moved using the robotic arm 128 or other suitable means. Therefore, the motion of the robotic arm 128 can move the end-effector assembly 136f over a large distance as an additional degree of freedom.

Figure 24:
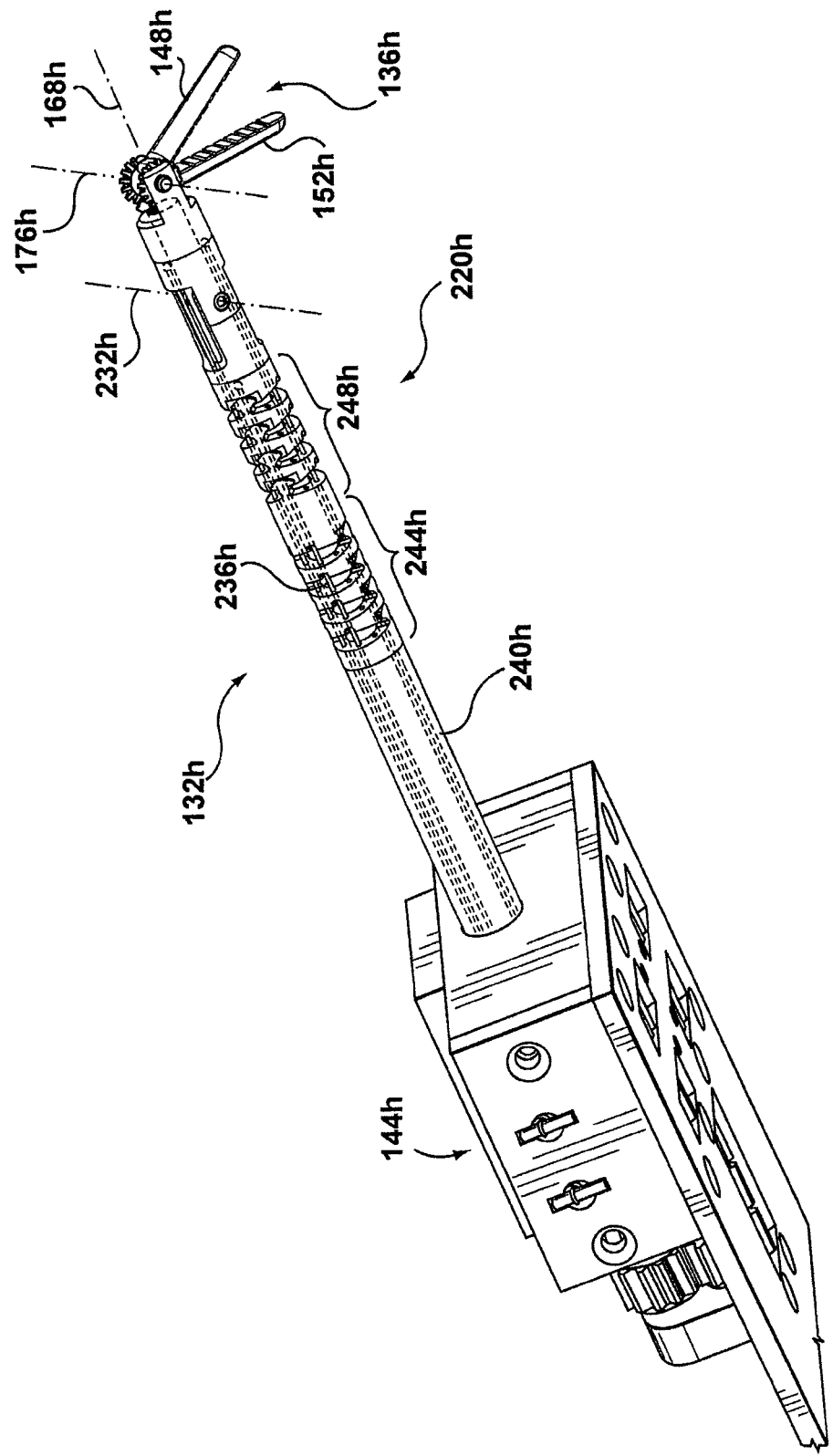
FIG. 24 is a perspective view of a robotic instrument in accordance with another embodiment.

Referring to FIG. 24, another embodiment of a robotic instrument 132h is shown. Like components of the robotic arm 132h bear like reference to their counterparts, except followed by the suffix "h". The robotic instrument 132h includes an end-effector assembly 136h, first, second, and third elongated elements (not shown) encased in a cover 240h, and a drive assembly 144h. In this particular embodiment, the robotic instrument 132h includes a flexible portion 220h configured to provide coarse motion proximate to the end-effector assembly 136h. The flexible portion 220h is located between the cover 240h and the end-effector assembly 136h.

The flexible portion 220h includes first and second subsections 244h and 248h. Each of the first and second subsections 244h and 248h is generally configured to bend within first and second coarse motion planes, respectively. It is to be understood that the first, second, and third elongated elements (not shown) are consequently bent when the first and second subsections 244h and 248h are bent such that the first, second, and third elongated elements can independently rotate while bent. Furthermore, the motion of the first subsection 244h and the second subsection 248h are independent such that one or both of the first and second subsections may be bent independently. Therefore, it is to be understood that the coarse motion of the robotic instrument 132h can be controlled using a set of at least one course motion adjustment cable 236h for each of subsection 244h and 248h by independently adjusting the tension of each set of at least one course motion adjustment cable.

Referring again to FIG. 24, in the present embodiment, the first and second coarse motion planes are substantially perpendicular to each other. However, it is to be appreciated that the first and second coarse motion planes do not need to be perpendicular to each other and can be at any angle in some embodiments. Furthermore, the exact configuration of first and second subsections 244h and 248h is not particularly limited. In the present embodiment, there are two subsections 244h and 248h. In other embodiments, it is to be understood that the flexible portion 220h can be modified to include more subsections to provide more coarse motion planes within which subsections of the flexible portion 220h can bend. In addition, the subsections need not be place adjacent to each other. Alternatively, it is also to be understood that the flexible portion 220h can be modified to include only one subsection to provide a single coarse motion plane.

In addition, the robotic instrument 132h includes an outer cover 240h. It is to be appreciated that the outer cover 240h can be rigid to provide support for the elongated elements (not shown) within the outer cover. In addition, the plurality of coarse motion adjustment cables 236h can be disposed within the outer cover 240h in a pace between the inside wall of the outer cover and the elongated elements. By placing the coarse motion adjustment cables 236h behind an outer cover, it is to be understood that wear on the cables is reduced. Furthermore, in the embodiment shown in FIG. 24, the outer cover 240h is fixed. That is, the outer cover 240h does not rotate. It will now be appreciated that when the robotic instrument 132h is inserted inside the patient P, the outer cover 240h reduces the chance of the robotic instrument 132h getting caught on something to cause damage.

It will now be appreciated that each subsection 244h and 248h will provide an additional degree of freedom. Referring back to FIG. 24, it will also now be apparent that the first and second subsections 244h and 248h add two more degrees of freedom to the robotic instrument 132h. Therefore, the robotic instrument 132h includes six degrees of freedom. The six degrees of freedom include the roll about the axis 168h (where the first, second, and third elongated elements rotate concurrently), rotation of the end-effector assembly 136h about a second axis 232h, rotation of a first working member 148h about a first axis 176h, rotation of a second working member 152h about the first axis 176h, the bending of the first subsection 244h and the bending of the second subsection 248h. In addition, the entire robotic instrument 132h can be moved on a rail system (not shown) to provide a seventh degree of freedom.

It is to be understood that by moving the first and second working members 148h and 152h together by rotating the first and second elongated elements, the working members 148h and 152h can rotate together about the first axis 176h such that the working members 148h and 152h can open and close over a range of angles about the first axis 176h. Furthermore, it will also be appreciated that to change the angle about the first axis 176h at which the working members 148h and 152h open and close, the first and second elongated elements rotate at a different amount compared with the third elongated element. This different amount is called a delta and can be adjusted to control the movement of the end effector assembly 136h relative to the robotic instrument 132h.

Figure 25:
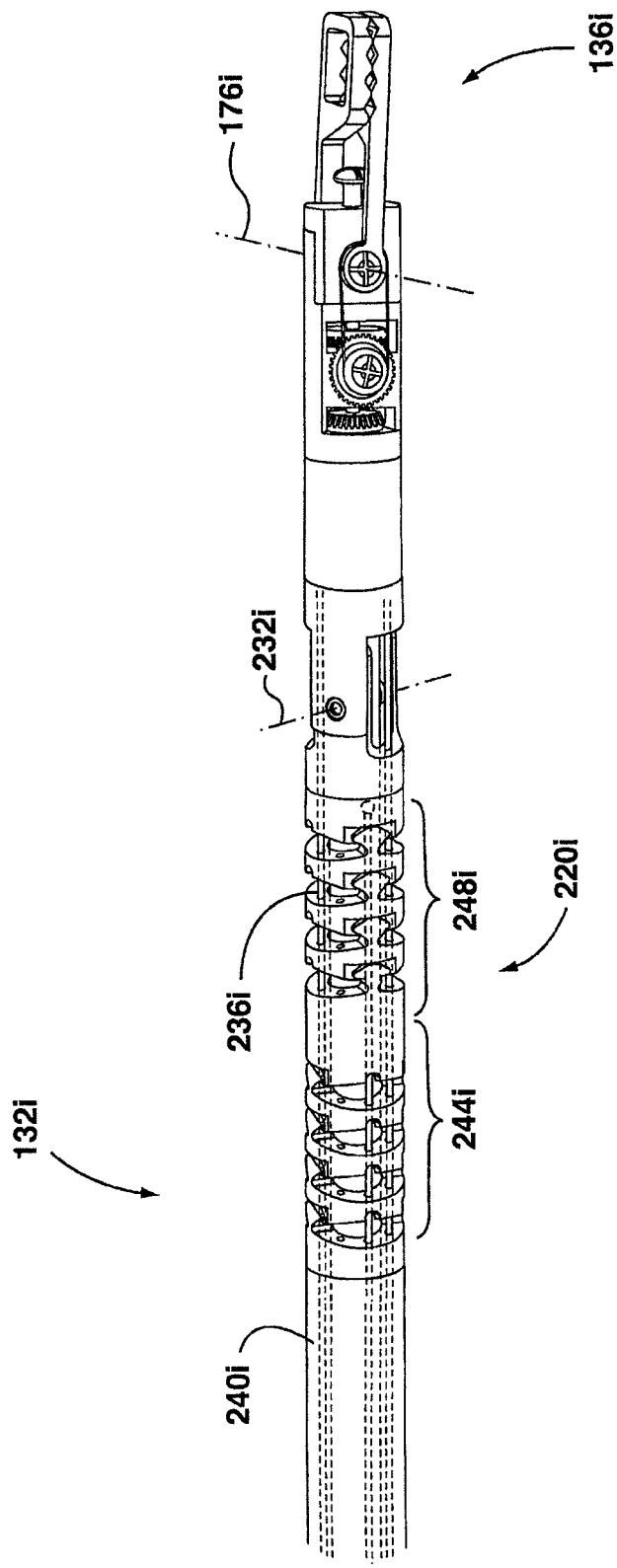
FIG. 25 is a perspective view of a portion of a robotic instrument in accordance with another embodiment.

Referring to FIG. 25, another embodiment of a robotic instrument 132i is shown. Like components of the robotic arm 132i bear like reference to their counterparts, except followed by the suffix "i". The robotic instrument 132i includes an end-effector assembly 136i, first, second, and third elongated elements (not shown) encased in a cover 240i, and a drive assembly 144i. In this particular embodiment, the robotic instrument 132i includes a flexible portion 220i configured to provide coarse motion proximate to the end-effector assembly 136i in a similar manner to the flexible portion 220h in the robotic instrument 132h. The flexible portion 220i is located between the cover 240i and the end-effector assembly 136i. The end-effector assembly 136i is similar to the end-effector assembly 136b described. Therefore, the robotic instrument 132i shown in FIG. 23 adds coarse motion to the end-effector assembly 136b.

Referring again to FIG. 22, it will now be appreciated that if the roll motion rotates the first axis 176g relative to the second axis 232g, the robotic instrument 132g would have positions where the first axis 176g can be parallel to the second axis 232g. However, in the embodiment shown in FIG. 25, the roll motion rotates both the first axis 176i and the second axis 232i by having the rotation occur between the flexible portion 220i and the second axis 232i. Therefore, the angle between the first axis 176h and the second axis 232i remains fixed. In the present embodiment, the angle between the first axis 176i and the second axis 232i is maintained at 90 degrees. However, in other embodiments, the angle can be greater or smaller than 90 degrees.

Therefore, it is to be understood that many combinations, variations and subsets of the embodiments and teachings herein are contemplated. As a non-limiting example, the robotic instrument 132d can be modified with the variation described in relation to the robotic instrument 132g to provide for coarse motion in the robotic instrument 132d. As another nonlimiting example, the robotic instrument 132 can be modified with the variation described in relation to the robotic instrument 132d to provide cauterizing functionality to the robotic instrument 132.

While specific embodiments have been described and illustrated, such embodiments should be considered illustrative only and should not serve to limit the accompanying claims.

What is claimed is:

1. A robotic surgical instrument, comprising:
   an end-effector assembly comprising a working member configured to pivot about a first axis;
   an elongated element extending between a proximal end and a distal end, the distal end being affixed with respect to the end effector assembly to hold the first axis perpendicular to the elongated element; and
   a second elongated element extending between a second proximal end and a second distal end, the second distal end of the second elongated element being coupled with the end effector assembly so that rotation of the second elongated element about a second axis pivots the working member about the first axis,
   wherein the elongated element and second elongated element are nested together and rotatable, and wherein the elongated element is a first tube, the second elongated element is a second tube, and the elongated element and second elongated element are nested together so that one of the first tube and the second tube is disposed within the other of the first tube and the second tube.

2. The robotic surgical instrument of claim 1, wherein the working member is a blade.

3. The robotic surgical instrument of claim 1, wherein the working member is configured to cauterize a tissue.

4. The robotic surgical instrument of claim 1, wherein one or both of the elongate member and the second elongate member comprises a flexible portion.

5. The robotic surgical instrument of claim 1, further comprising an electrical wire extending through the second elongated element and coupled to the working member.

6. The robotic surgical instrument of claim 1, wherein the second distal end of the second elongated element is coupled to the working member of the end-effector assembly via a gear.

7. A robotic surgical instrument, comprising:
an end-effector comprising a working member configured to pivot about a first axis;
an elongated element extending between a proximal end and a distal end, the distal end being coupled to the end effector to hold the first axis perpendicular to the elongated element; and
a second elongated element extending between a second proximal end and a second distal end, the second distal end of the second elongated element being coupled with the end effector so that rotation of the second elongated element about a second axis pivots the working member about the first axis,
wherein the elongated element and second elongated element are nested together and rotatable relative to each other, and wherein the elongated element is a first tube, the second elongated element is a second tube, and the elongated element and second elongated element are nested together so that one of the first tube and the second tube is disposed within the other of the first tube and the second tube.

8. The robotic surgical instrument of claim 7, wherein the working member is a blade.

9. The robotic surgical instrument of claim 7, wherein the working member is configured to cauterize a tissue.

10. The robotic surgical instrument of claim 7, wherein one or both of the elongate member and the second elongate member comprises a flexible portion.

11. The robotic surgical instrument of claim 7, wherein the second distal end of the second elongated element is coupled to the working member of the end-effector assembly via a gear.

12. A robotic surgical system, comprising:
a support arm; and
a surgical instrument coupled to the support arm, the surgical instrument comprising:
an end-effector assembly comprising a working member configured to pivot about a first axis,
an elongated element extending between a proximal end and a distal end, the distal end being affixed with respect to the end effector assembly to hold the first axis perpendicular to the elongated element, and
a second elongated element extending between a second proximal end and a second distal end, the second distal end of the second elongated element being coupled with the end effector assembly so that rotation of the second elongated element about a second axis pivots the working member about the first axis,
wherein the elongated element and second elongated element are nested together and rotatable, and wherein the elongated element is a first tube, the second elongated element is a second tube, and the elongated element and second elongated element are nested together so that one of the first tube and the second tube is disposed within the other of the first tube and the second tube.

13. The robotic surgical system of claim 12, wherein the surgical instrument is movably coupled to the support arm.

14. The robotic surgical system of claim 12, wherein the support arm is a robotic arm configured to move in response to an input control signal received from an input device operated by a user.

15. The robotic surgical system of claim 12, wherein the working member is a blade.

16. The robotic surgical instrument of claim 12, wherein the working member is configured to cauterize a tissue.

17. The robotic surgical instrument of claim 12, wherein one or both of the elongate member and the second elongate member comprises a flexible portion.

18. The robotic surgical instrument of claim 12, further comprising an electrical wire extending through the second elongated element and coupled to the working member.

19. The robotic surgical instrument of claim 12, wherein the second distal end of the second elongated element is coupled to the working member of the end-effector assembly via a gear.

* * * * *

UNITED STATES PATENT AND TRADEMARK OFFICE
CERTIFICATE OF CORRECTION

| | |
|---|---|
| PATENT NO. | : 11,872,694 B2 |
| APPLICATION NO. | : 18/164479 |
| DATED | : January 16, 2024 |
| INVENTOR(S) | : Eric Butt et al. |

It is certified that error appears in the above-identified patent and that said Letters Patent is hereby corrected as shown below:

In the Specification

On Column 10, Line 41: Delete "14 0a" and insert -- 140a --.

On Column 10, Line 48: Delete "and." and insert -- and --.

On Column 17, Line 55: Delete "136f" and insert -- 136f. --.

On Column 17, Line 56: Delete "140f" and insert -- 140f. --.

On Column 17, Line 60: Delete "232f" and insert -- 232f. --.

On Column 17, Line 64: Delete "176f" and insert -- 176f. --.

On Column 18, Line 3: Delete "168f" and insert -- 168f. --.

Signed and Sealed this
Twenty-sixth Day of March, 2024

*Katherine Kelly Vidal*
Katherine Kelly Vidal
*Director of the United States Patent and Trademark Office*